(12) United States Patent
Pedersen et al.

(10) Patent No.: US 10,773,029 B2
(45) Date of Patent: Sep. 15, 2020

(54) MEDICAL INJECTION DEVICE WITH NEEDLE CLEANING

(71) Applicant: Novo Nordisk A/S, Bagsvaerd (DK)

(72) Inventors: Simon Munch Pedersen, Copenhagen N (DK); Lars Eilertsen, Fredensborg (DK); Morten Revsgaard Frederiksen, Copenhagen K (DK); Ruben Archilla, Copenhagen NV (DK); Mattias Ingerslev, Copenhagen OE (DK); Bo Radmer, Hilleroed (DK); Rasmus Kann Jensen, Lyngby (DK); Kurt Solgaard, Graested (DK)

(73) Assignee: Novo Nordisk A/S, Bagsvaerd (DK)

( * ) Notice: Subject to any disclaimer, the term of this patent is extended or adjusted under 35 U.S.C. 154(b) by 75 days.

(21) Appl. No.: 16/303,426

(22) PCT Filed: Jun. 20, 2017

(86) PCT No.: PCT/EP2017/065048
§ 371 (c)(1),
(2) Date: Nov. 20, 2018

(87) PCT Pub. No.: WO2018/001790
PCT Pub. Date: Jan. 4, 2018

(65) Prior Publication Data
US 2019/0282767 A1    Sep. 19, 2019

(30) Foreign Application Priority Data

Jun. 30, 2016 (EP) .................................... 16177273
Sep. 14, 2016 (EP) .................................... 16188751

(51) Int. Cl.
*A61M 5/32* (2006.01)
*A61M 5/20* (2006.01)
(Continued)

(52) U.S. Cl.
CPC ............ *A61M 5/3202* (2013.01); *A61M 5/00* (2013.01); *A61M 5/20* (2013.01); *A61M 5/315* (2013.01);
(Continued)

(58) Field of Classification Search
CPC ...... A61M 5/178; A61M 5/31; A61M 5/3205; A61M 5/321; A61M 5/00; A61M 5/20;
(Continued)

(56) References Cited

U.S. PATENT DOCUMENTS 3,354,881 A    11/1967  Bloch
4,416,663 A    11/1983  Hall
(Continued)

FOREIGN PATENT DOCUMENTS

WO    2014029018 A1    2/2014
WO    2014064100 A1    5/2014
(Continued)

*Primary Examiner* — Jason E Flick
(74) *Attorney, Agent, or Firm* — Wesley Nicolas

(57) ABSTRACT

The invention relates to a prefilled injection pen for apportioning multiple set doses of a liquid drug. The injection pen comprises a housing assembly with a removable cap rotatable coupled to the housing assembly such that the user has to rotate the removable cap upon mounting and dismounting the removable cap. Rotation of the removable cap initiates a process in which the proximal end of a needle cannula is first inserted into a cartridge permanently embedded in the housing assembly and thereafter moves the cartridge proximally to thereby pump a predetermined amount of the preservative containing liquid drug from the cartridge and into a cleaning chamber carried by an axially movable shield. The needle cannula is mounted in a needle hub which is arranged to follow rotation of the removable cap and guided helically in relation to the housing assembly such that the needle hub is moved proximally upon rotation of the removable cap. Further, the axially movable shield is oper-
(Continued)

ated by the needle hub to follow proximal movement of the needle hub such that the distal tip of the needle cannula is maintained inside the cleaning chamber upon axil movement of the needle hub and the needle cannula.

15 Claims, 20 Drawing Sheets

(51) Int. Cl.
    *A61M 5/315*      (2006.01)
    *A61M 5/34*      (2006.01)
    *A61M 5/00*      (2006.01)

(52) U.S. Cl.
    CPC ............... *A61M 5/32* (2013.01); *A61M 5/34* (2013.01); *A61M 5/322* (2013.01)

(58) Field of Classification Search
    CPC ...... A61M 5/315; A61M 5/32; A61M 5/3202; A61M 5/322; A61M 5/34
    See application file for complete search history.

(56) References Cited

U.S. PATENT DOCUMENTS

| | | |
|---|---|---|
| 4,666,436 A | 5/1987 | McDonald et al. |
| 2015/0273161 A1* | 10/2015 | Bengtsson ............ A61M 5/001 604/198 |
| 2016/0001014 A1* | 1/2016 | Eilertsen ............... A61M 5/346 604/198 |
| 2016/0271319 A1* | 9/2016 | Bengtsson .............. A61M 5/24 |

FOREIGN PATENT DOCUMENTS

| | | |
|---|---|---|
| WO | 2015062845 A1 | 5/2015 |
| WO | 2016173895 A1 | 11/2016 |

\* cited by examiner

MEDICAL INJECTION DEVICE WITH NEEDLE CLEANING

CROSS-REFERENCE TO RELATED APPLICATIONS

This application is a 35 U.S.C. § 371 National Stage application of International Application PCT/EP2017/065048, filed Jun. 20, 2017, which claims priority to European Patent Applications 16177273.6, filed Jun. 30, 2016 and 16188751.8, filed Sep. 14, 2016, the contents of all above-named applications are incorporated herein by reference.

THE TECHNICAL FIELD OF THE INVENTION

The invention relates to a medical injection device for injecting a liquid drug and especially to a pre-filled injection device for apportioning a multiple number of individual settable doses. The invention especially relates to such pen-shaped and pre-filled injection device wherein the same needle cannula is used for a number of subsequent injections and wherein the distal tip of the needle cannula is cleaned between subsequent injections.

DESCRIPTION OF RELATED ART

Injection devices wherein the tip of the needle cannula is maintained in a cleaning solvent between subsequent injections are disclosed in e.g. U.S. Pat. No. 4,416,663 and in U.S. Pat. No. 4,666,436. As can be seen from these prior art injection devices, the cleaning chamber is usually carried distally on a retractable shield covering the distal tip of the needle cannula between subsequent injections.

Further WO2014/064100 discloses a pre-filled disposable injection device which has an axially movable shield covering the distal tip of the needle cannula between subsequent injections. This axially movable shield is urged into a distal covering position by a spring. Further, in one embodiment, the shield is provided with a hollow chamber containing a liquid cleaning solvent such as a chemical disinfectant or biocide which cleans the tip of the needle cannula between subsequent injections.

Examples on such cleaning solvents are provided in WO 2014/029018. However, as disclosed in WO 2015/062845 it is preferred to use the preservative contained in the liquid drug as the cleaning solvent. This is in one example done by filling the cleaning chamber with preservative containing liquid drug directly from the cartridge embedded in the pre-filled injection device to thereby utilize a quantum of the preservative containing liquid drug as the cleaning solvent.

The filling of the cleaning chamber from the cartridge is in WO 2015/062845 done by having the protective cap being coupled to the injection device such that at least the distal part of the injection device including the cartridge is forced to move proximally as a consequence of the user rotating the protective cap.

International Patent Application PCT/EP2016/058722 filed Apr. 20, 2016 discloses a prefilled injection device which is sold to the user with the needle cannula disconnected from the cartridge. In order to insert the proximal end of the needle cannula into the cartridge, the user rotates the removable cap which in turn rotates the axially movable shield and with it also the needle hub. As the needle hub rotates it screws along a helical track provided in an intermediate member which intermediate member also moves the cartridge proximally to thereby pump a quantum of the liquid drug inside the cartridge into a cleaning chamber carried by the axially movable shield.

In an injection device of the disclosed type it is important to maintain the distal tip of the needle cannula inside the boundaries of the cleaning chamber when not injecting in order to prevent the distal tip of the needle cannula from being contaminated.

This is especially cumbersome when the injection device is delivered without the needle cannula inserted into the interior of the cartridge since the distal tip of the needle cannula needs to be maintained inside the cleaning chamber during insertion of the needle cannula into the cartridge.

DESCRIPTION OF THE INVENTION

It is an object of the present invention to provide an injection device which simplifies the insertion of the needle cannula into the cartridge and which links the axial movement of the needle cannula to the movement of the axially movable shield in a simple and robust manor.

Accordingly, in a general aspect of the present invention a prefilled injection pen for apportioning multiple set doses of a liquid drug comprises:

A housing assembly made from one or more parts which together forms the outer parameters of the injection pen. Distally the housing assembly supports a removable cap which is rotatable in relation to the housing assembly. The housing assembly further encapsulates the piston rod drive system used for driving out liquid drug from the injection pen. The removable cap preferably covers and protects the distal part of the housing assembly between injections.

A non-replaceable cartridge permanently embedded in the housing assembly and having an interior containing a preservative containing liquid drug. The interior of the cartridge lies between a distal septum and a movable plunger which plunger abuts the piston rod drive system or at least a piston rod of the piston rod drive system. During dosing the piston rod moves in the distal direction thereby moving the plunger distally inside the cartridge.

A needle cannula secured in a needle hub which needle cannula has a distal end with a distal tip, a proximal end and a lumen there between.

An axially movable shield which is to be moved from an extended position in which the axially movable shield covers or shields at least the distal tip of the needle cannula to a retracted position in which at least the distal tip of the needle cannula is exposed and which axially movable shield carries a cleaning chamber for containing therein a quantum of the preservative containing liquid drug.

According to the present invention, the needle hub is arranged to follow rotation of the removable cap such that the needle hub rotates relatively to the housing assembly when the removable cap is rotated relatively to the housing assembly. However, the rotational speed of the needle hub and the removable cap can be different and the engagement causing the rotation can be made in many ways, both direct and indirect. In one particular example an axially movable shield is present between the removable cap and the needle hub. During the rotation of the removable cap and hence the needle hub, the needle hub is further guided helically in relation to the housing assembly such that the needle hub is moved proximally upon rotation of the removable cap. The axially movable shield and the needle hub engage each other and the needle shield is operated by the needle hub such that the axially movable shield carrying the cleaning chamber follows the proximal movement of the needle hub either in a rotational or linear movement.

As the needle hub is moved helically in order to insert the proximal end of the needle cannula into the cartridge, the needle shield follows the movement of the needle hub at least in the axial direction such that the distal tip although being moved axially is maintained inside the cleaning chamber as the needle shield that carries the cleaning chamber is operated to move by the needle hub.

In earlier solutions the needle hub is guided in one helical track and the shield is guided in a different helical track which makes such solution complicated since these helical tracks have to be aligned in order to maintain the distal tip of the needle cannula inside the cleaning chamber as the needle hub and the shield travels in the proximal direction.

However, by confining the helical movement to only the needle hub and to have the axially movable shield simply being operated proximally by the needle hub a very simple and robust solution is provided. In that respect a very simple solution would be to simply have the axially movable shield be a slave to the needle hub such that the needle hub has an engagement means such as a hook or the like that engages the axially movable shield in order to make the axially movable shield follow proximal movement of the needle hub.

In that respect "covers or shields" the distal tip of the needle cannula means that the axially movable shield extends at least to the most distal tip of the needle cannula. The distal surface of the axially movable shield obviously has an opening for the distal tip of the needle cannula to be exposed during injection. Further, the axially movable shield can be made from a plurality of parts. One part could e.g. be a cleaning unit carrying the cleaning chamber which thus could be the part covering the distal end of the needle cannula. By axially movable is meant that the axially movable shield moves in the longitudinal direction of the pen along the centre line X. The axially movable shield preferably telescopes into or onto the housing assembly.

In one example, the cartridge holder, being a part of the housing assembly, has one or more preferably radial protrusions provided thereon. These protrusions engage one or more helical tracks provided in the needle hub such that the needle hub screws helically when rotated relatively to the housing assembly. It is also possible to provide the helical track in the housing assembly and the protrusions on the needle hub.

As the needle hub is rotated helically in the proximal direction, the needle hub engages and moves the cartridge also in the proximal direction. For this purpose, the needle hub is preferably provided with a number of legs or other axial extensions which engages on the distal top of the cartridge in order to push the cartridge in the proximal direction. However, the engagement can be to any physical part of the cartridge A cartridge for a liquid drug as often used in the pharmaceutical industry usually has a penetreble septum provided at the distal end. This septum is usually secured by a metal skirt which is rolled, pressed or folded to the distal end of the cartridge.

In one example, the axial extension on the needle hub abuts on the distal end of this metal skirt to move the cartridge in the proximal direction.

Further, the movable plunger inside the cartridge rest against the piston rod system wherein a piston rod, with or without a piston rod foot, abuts the plunger. Since the piston rod is prevented from moving in the proximal direction pressure is build up inside the cartridge as the cartridge itself is moved proximally. Due to this pressure build up, a predetermined quantum of the preservative containing liquid drug is forced through the lumen of the needle cannula and into the cleaning chamber carried by the axially movable shield.

The axially movable shield is preferably arranged between the removable cap and the needle hub in a radial cross section. In one example, the axially movable shield engages the needle hub such that the needle hub rotates simultaneously with the axially movable shield.

For the purpose of rotating the removable cap to mount and/or to dismount the removable cap from the housing assembly, the removable cap is preferably provided with a helical cap track engaging protrusions provided on the housing assembly. Here any number of tracks and protrusions can be provided. The protrusions preferably extend radially from the housing assembly. However, as kinematic reversible is obvious, the protrusions could be provided inside the removable cap and the tracks be provided on the housing assembly. Further, the removable cap only covers a part of the housing assembly when mounted. The part covered by the removable cap is usually the part or end of the housing assembly carrying the needle cannula i.e. the distal part.

The usual operation of an injection device requires the user to remove the removable cap before performing an injection and to mount the removable cap onto the injection device after the injection. The removable cap can either be moulded as one single part or be manufactured form two or more parts permanently connected together to operate in unison as a removable cap. The removable cap usually covers the distal part of the injection device between injections and can obviously cover more or less of the injection device. It is also customary to provide the removable cap with a clip for carrying the injection device with the removable cap in a shirt pocket.

In one further example the removable cap engages the axially movable shield such that a rotation of the removable cap is transferred to a rotation of the axially movable shield. The rotational movement is preferably transferred via an engagement between ribs abutting each other.

As the user rotates the removable cap relatively to the housing this rotation is transferred to a rotation of the axially movable shield and in turn to a rotation of the needle hub which henceforth screws helically in the proximal direction in relation to the housing assembly such that the proximal part of the needle cannula is inserted through the septum of the cartridge and into the interior of the cartridge whereby the preservative containing liquid drug can flow through the lumen of the needle cannula.

Before performing an injection it is important to vent the liquid system. This is preferably done by moving the axially movable shield a predetermined distance in the proximal direction such that at least the distal tip of the needle cannula is penetrated through the distal septum of the cleaning chamber. Once the distal tip of the needle cannula has just penetrated through the distal septum of the cleaning chamber and is positioned just outside the cleaning chamber the pressure inside the cartridge aligns with that of the surroundings.

In order to retract the axially movable shield a little distance to allow the distal tip to penetrate out from the cleaning chamber, the housing assembly, preferably the cartridge holder or other part of the housing assembly is provided with a helical flange which can guide the axially movable shield which shield for that purpose is provided with a first protrusion.

As the shield is rotated by the user, this first protrusion engages the helical flange on the cartridge holder such that the axially movable shield moves proximally in a helical movement.

Further, a second protrusion is provided to convey rotational movement from the axially movable shield to the needle hub. However, such rotational movement can also be transferred in alternatives way, e.g. by providing a friction between the axially movable shield and the needle hub such that the needle hub follows rotation of the shield.

In one example wherein the user rotates the removable cap which in turn rotates the axially movable shield, this rotation is transferred to a rotation of the needle hub, preferably by an engagement between the second protrusion on the inner surface of the shield engaging and driving a rib or other surface on the needle hub.

In a further example, the second protrusion inside the axially movable shield is rotational guided in a radial track provided in the needle hub. This radial track allows the needle hub and the axially movable shield to rotate in relation to each other but couples the axially movable shield to translate proximally together with the needle hub as the needle hub moves in the proximal direction. The radial track is preferably provided with an opening allowing the second protrusion to escape from the radial track and thus decouple the axial movement of the shield from the movement of the needle hub.

In a further example, the axially movable shield is provided with a longitudinal slit and the housing assembly provided with an internal rib. When this longitudinal slit and the rib are not aligned it is not possible to move the axially movable shield in the proximal direction. However upon rotation of the axially movable shield, the longitudinal slit can be brought into alignment with the internal rib of the housing assembly thus allowing telescopic movement of the axially movable shield.

As the user manually rotates the axially movable shield, the first protrusion inside the axially movable shield travels along the helical flange on the housing assembly such that the axially movable shield is moved in the proximal direction and at the same time is the longitudinal slit brought into alignment with the internal rib of the housing. The distal tip of the needle cannula is thus brought to a position in front of the cleaning chamber to vent the liquid system and the axially movable shield in unlocked and positioned in a position ready to perform an injection.

The user can hereafter perform the injection automatically by pressing the axially movable shield against the skin as is commonly known from shield triggered injection devices. The force needed to drive the liquid drug from the cartridge is preferably delivered by a spring engine.

As the cleaning chamber is filled with liquid drug from the cartridge in the described initiation process, the air contained inside the cleaning chamber should be allowed to escape from the cleaning chamber during filling. Further, the different tolerances applying sometimes makes the volume filled into the cleaning chamber larger than the volume of the cleaning chamber. It is therefore also desirable to provide a possibility for overfilling the cleaning chamber without creating an overpressure inside the cleaning chamber.

The cleaning chamber is therefore provided with an opening through which air and liquid can flow during filling and which is sealed after the cleaning chamber has been filled.

For the purpose of closing this opening a valve is provided. This valve is open during filling of the cleaning chamber but permanently closed once the cleaning chamber has been filled. In order to close the valve after filling of the cleaning chamber, the needle hub is provided with a longitudinal rib which engages the valve.

During the initiation process the needle hub is rotated to a position wherein the needle hub locks to the housing assembly. Once the needle hub is locked and secured, a continued rotation of the shield carrying the cleaning chamber will also rotate the valve together with the shield and the cleaning chamber. However, due to engagement with the now locked and secured needle hub, the valve is actually prevented from rotating such that only the shield and the cleaning chamber rotate relatively to the valve thus bringing the valve to the closed position. Such valve is further described in details in WO 2017/050694.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and preferably connected to a needle hub to form a complete injection needle, all though the needle cannula could also be connected directly to the housing structure without a needle hub. A needle cannula could however also be made from a polymeric material or a glass material.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

"Cleaning chamber" is in the present description broadly meant to be any kind of reservoir containing a cleaning solvent to clean at least the distal tip of the needle cannula between subsequent injections. Such cleaning chamber is preferably both distally and proximally sealed by a pierceable septum. However, the proximal septum could be replaced by any kind of sealing which would seal against the outer surface of the needle cannula. The distal septum and the proximal septum or seal of the cleaning chamber defines a confinement containing the cleaning solvent which cleaning solvent in a preferred embodiment is identical to the preservatives contained in the liquid drug used in the specific injection device. In a most preferred solution, the same preservative containing liquid drug is present in both the cleaning chamber and in the cartridge of the injection device thereby avoiding contamination of the preservative containing drug inside the cartridge. Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the predetermined amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

The term "Permanently connected" as used in this description is intended to mean that the parts, which in this application is embodied as a cartridge and a housing assembly, requires the use of tools in order to be separated and should the parts be separated it would permanently damage at least one of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and usually carrying the dose dial button.

Figure 1:
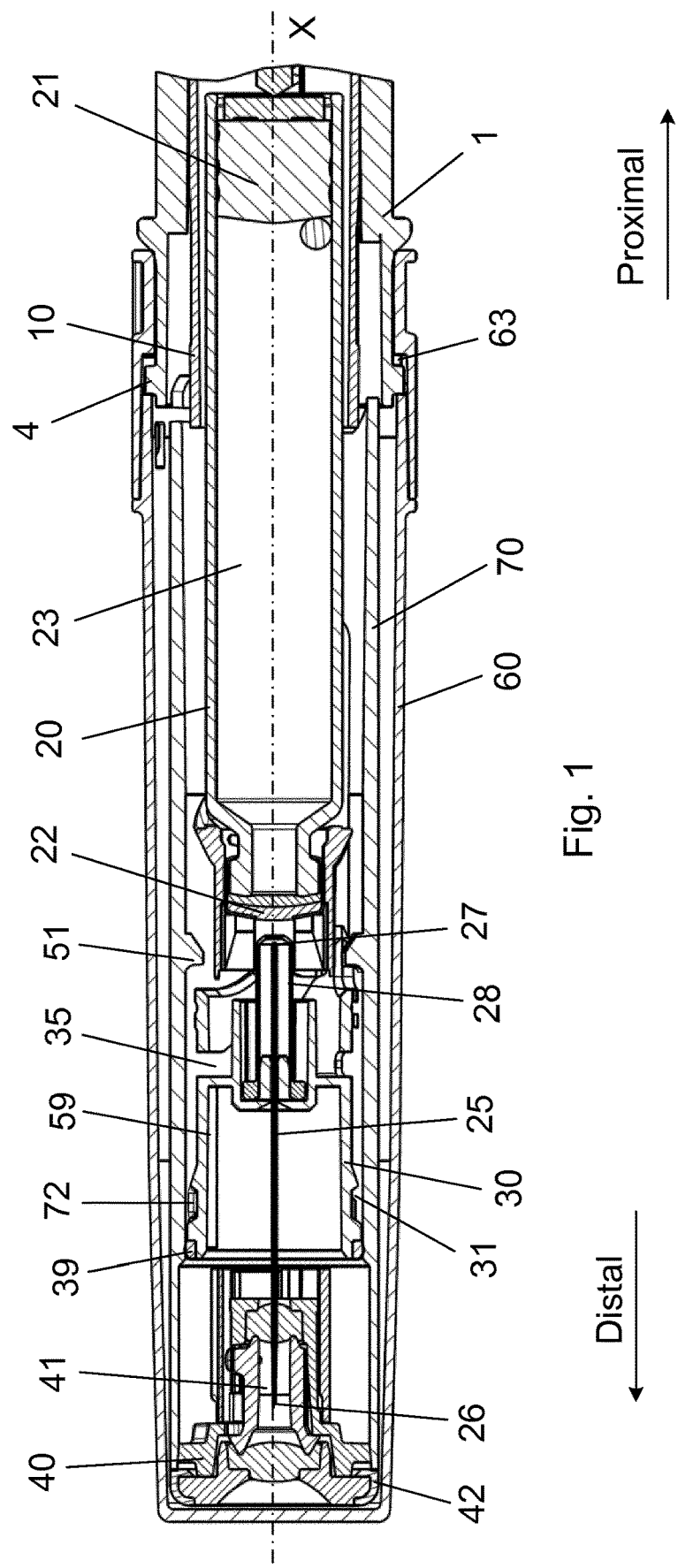
FIG. 1 show a cross sectional view of the front end of the injection device before the initiation process is started.

Distal and proximal are meant to be along an axial orientation extending along the longitudinal axis "X" of the injection device as further indicated in FIG. 1 which discloses the front end of the injection device according to a first embodiment.

The outer shell of the injection device is made up from a housing assembly which comprises a housing base 1 and a cartridge holder 10 which are permanently and irreversible coupled together to form the housing assembly. The housing assembly can also include further elements.

Figure 2:
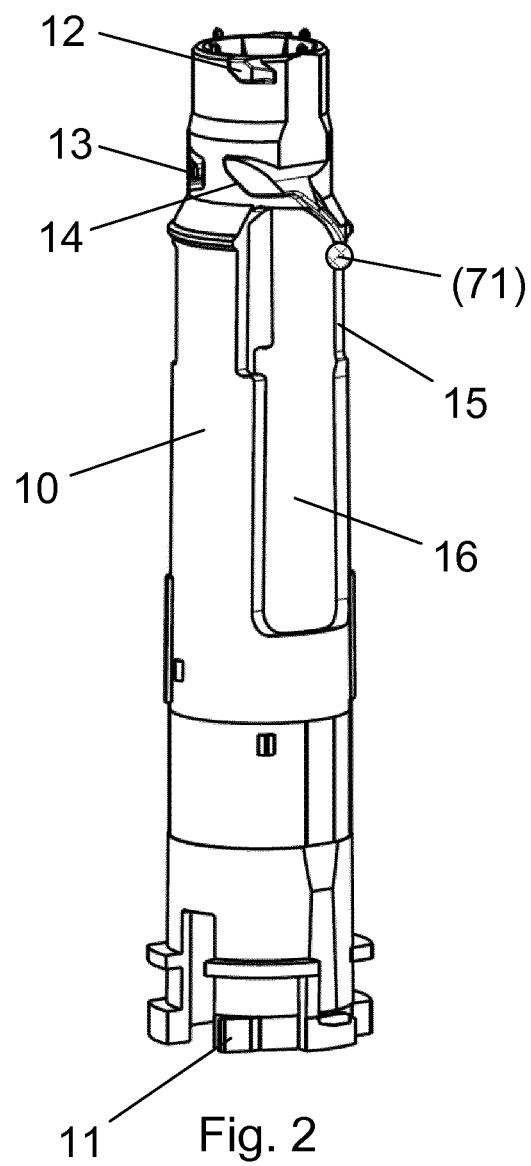
FIG. 2 show a perspective view of the cartridge holder.
Figure 3:
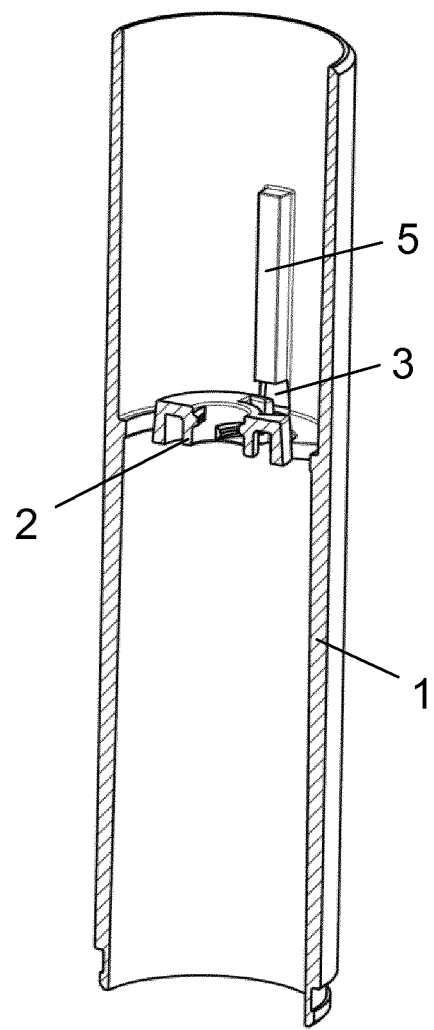
FIG. 3 show a cross sectional view of the housing base.

The cartridge holder 10 is shown in details in FIG. 2 and is proximally provided with a click arm 11 which clicks into the housing base 1 disclosed in FIG. 3 to form one housing assembly. The cartridge holder 10 is further provided with a protrusion 12, a helical guiding flange 14 and a flexible locking arm 13 as will be explained.

The interior of the housing base 1 is disclosed in FIG. 3. Internally the housing base 1 is provided with a threaded nut member 2 which is either formed as a separate part inserted into the housing base 1 or as disclosed as a unitary and integral moulded part of the housing base 1. The housing base 1 further has an opening 3 for irreversible receiving the click arm 11 of the cartridge holder 10 to form one unitary housing assembly.

As seen in FIG. 1, a cartridge 20 is secured between the cartridge holder 10 and the housing base 1. The cartridge 20 is proximally provided with a movable plunger 21 and distally provided with a membrane or septum 22. The interior 23 of the cartridge 20 defined between the plunger 21 and the septum 22 holds the liquid drug to be injected.

In FIG. 1, the needle cannula 25 has not yet been inserted through the septum 22 of the cartridge 20 and the needle hub 30 carrying the needle cannula 25 is thus located in a distal position on the cartridge holder 10 as will be explained.

The needle cannula 25 has a distal tip 26 and a proximal end 27 and a hollow lumen 29 there between. The distal tip 26 is further inserted into a cleaning chamber 41 of a cleaning module 40 which is carried by an axially movable shield 70.

In the position disclosed in FIG. 1, the cleaning chamber 41 is empty and sterile. Further, the proximal end 27 of the needle cannula 25 is maintained inside a bag 28 which is also sterile at its inside.

A first sterility barrier 39 is provided between the needle hub 30 and the axially movable shield 70 and a second sterility barrier 42 is located between the cleaning module 40 and the axially movable shield 70. Since these two sterility barriers 39, 42 seals against the axially movable shield 70, the internal area containing the distal part of the needle cannula 25 and the cleaning chamber 41 can henceforth be maintained sterile until first use.

Figure 4:
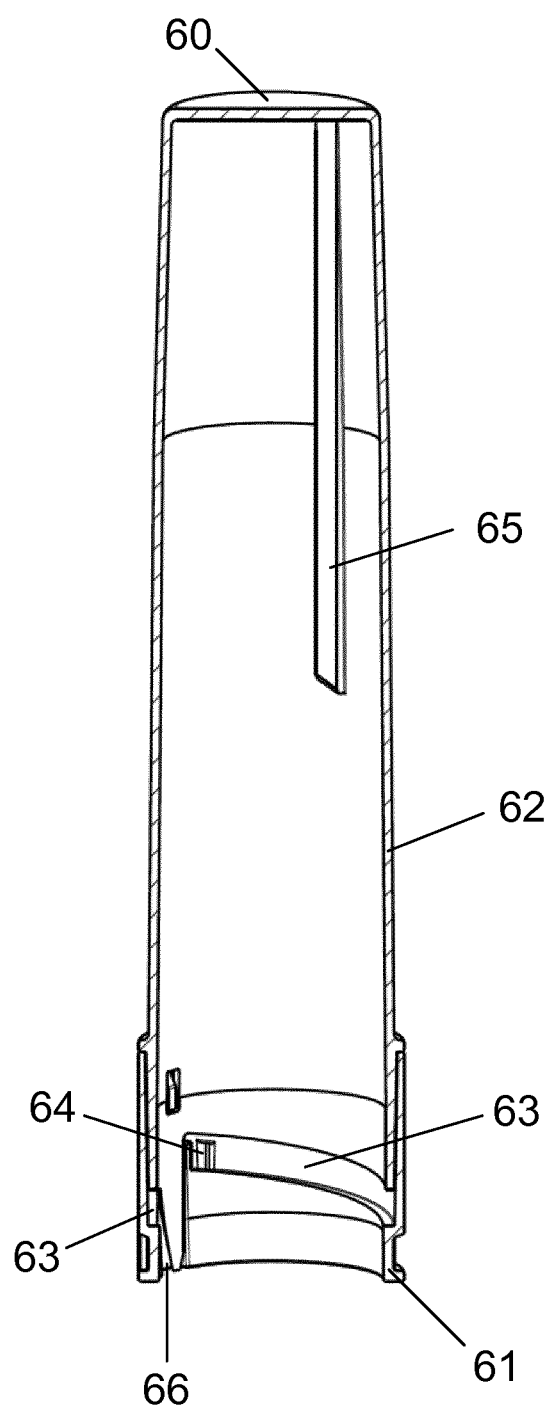
FIG. 4 show a cross sectional view of the removable cap.

The front end of the injection device is on the outside covered by a removable cap 60 which is further disclosed in FIG. 4. This removable cap 60 comprises a first part 61 and a second part 62 which are click fitted together and defines a helical cap track 63 located between the first part 61 and the second part 62. Preferably two such tracks 63 are provided.

The removable cap 60 is on the inner side provided with a longitudinal rib 65 which engages an outwardly pointing rib 75 provided on the outer surface of the axially movable shield 70 as will be explained. These ribs 65, 55 are preferably provided in pairs.

When the removable cap 60 is mounted onto the front end of the injection device as disclosed in FIG. 1, the helical cap track 63 of the removable cap 60 engages a pair of radial protrusions 4 provided on an outer surface of the housing base 1. The helical cap track 63 of the removable cap 60 is at one end of the helical cap track 63 provided with a stop protrusion 64 over which the protrusions 4 click to secure the removable cap 60 on the housing base 1. The opposite end of the helical cap track 63 ends in a track opening 66 through which the protrusion 4 moves when the removable cap 60 is mounted onto the housing base 1. Since the protrusions 4 operates in the helical cap track 63, a user is forced to rotate the removable cap 60 relatively to the housing base 1 in order to remove the removable cap 60.

Figure 5:
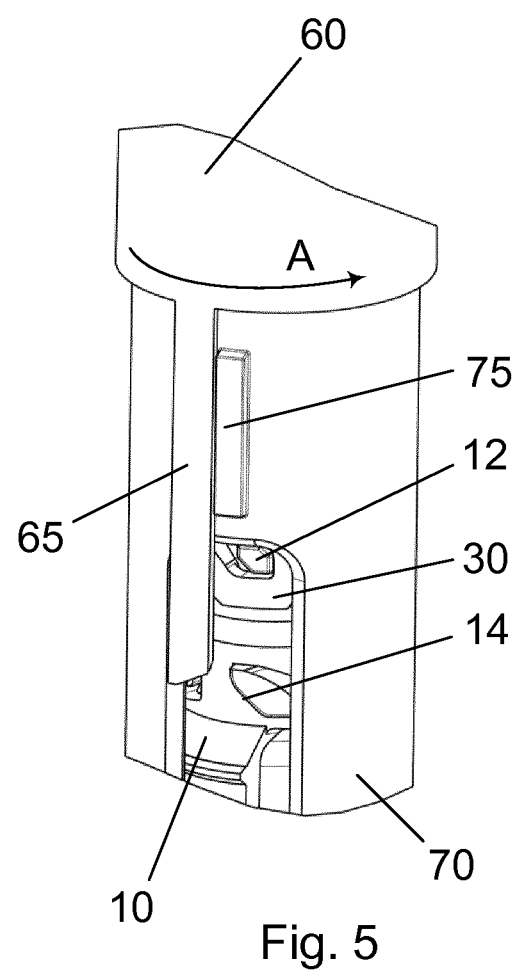
FIG. 5 show a detail of the engagement between the removable cap and the axially movable shield.

As best seen in FIG. 5 such rotation of the removable cap 60 is transformed to a similar rotation of the axially movable shield 70 since the longitudinal rib 65 inside the removable cap 60 engages the outwardly pointing rib 75 provided on the axially movable shield 70. In FIG. 5 a part of the removable cap 60 has been visually cut away in order to view the engagement between the longitudinal rib 65 and the outwardly pointing protrusion 55. The removable cap 60 is in the disclosed embodiment meant to be rotated in an anti-clockwise direction as indicated by the arrow "A" in FIG. 5.

Figures 6, 7:
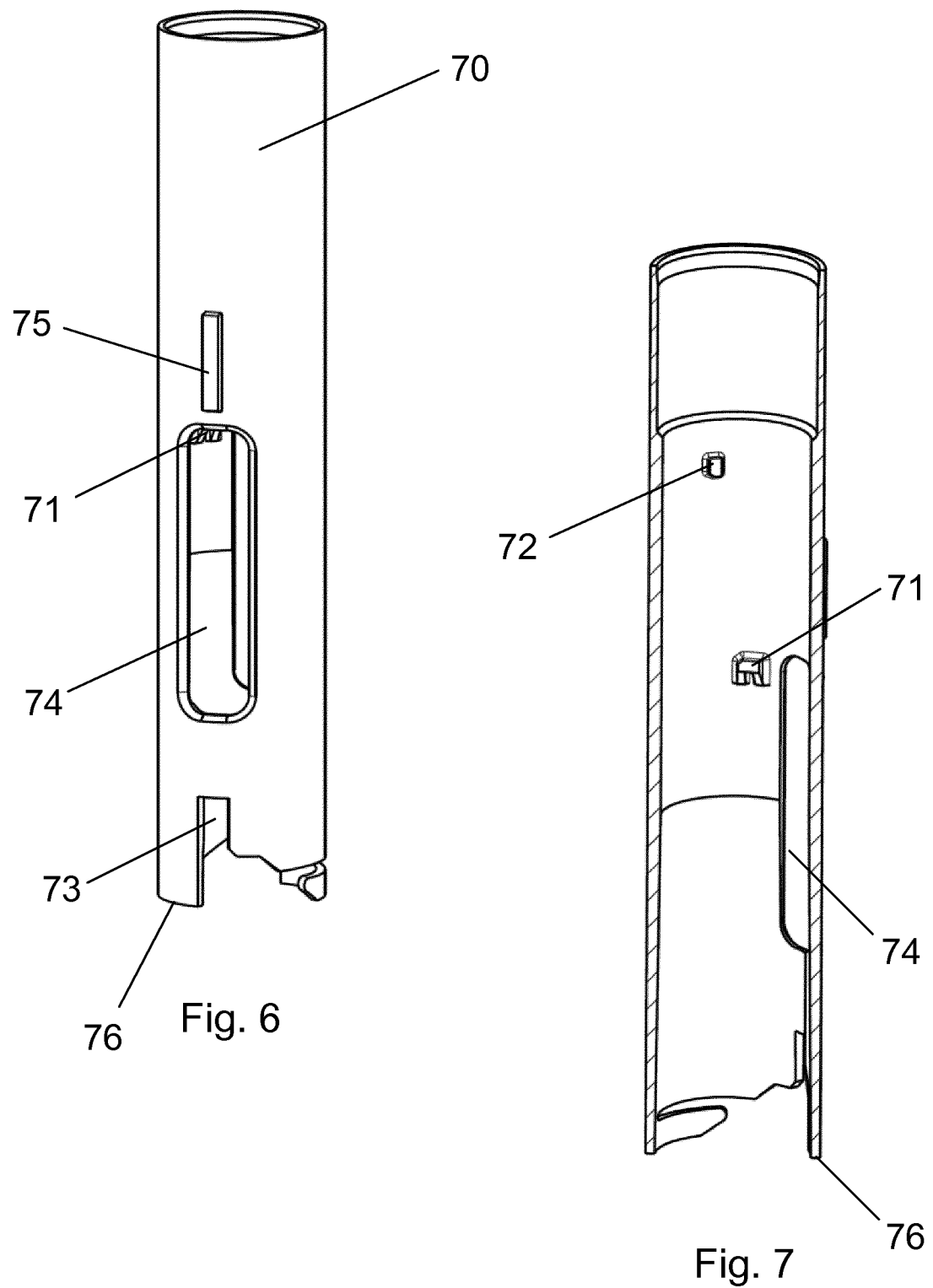
FIG. 6 show a perspective view of the axially movable shield.
FIG. 7 show a cross sectional view of the axially movable shield.

The axially movable shield 70 is shown in details in FIG. 6 and in FIG. 7, where FIG. 7 is a view to the inner surface of the axially movable shield 70. On the inner surface a first protrusion 71 and a second protrusion 72 are provided. Both these protrusion 71, 72 can be provided in any random number both are preferably provided in pairs. Further, the axially movable shield 70 is at the proximal end provided with a longitudinal slit 73 which fits over an internal rib 5 provided inside the housing base 1 as best seen in FIG. 3, the purpose of which will be explained later in conjunction with FIG. 19.

The sidewall of the axially movable shield 70 is further provided with a longitudinal window or opening 74 through which the user can inspect the content of the cartridge 20.

When the user receives the injection device, the proximal end 27 of the needle cannula 25 is not inserted into the cartridge 20 and the cleaning chamber 41 is empty and sterile as disclosed in FIG. 1. The initial steps of inserting the needle cannula 25 in the cartridge 20 and filling liquid drug into the cleaning chamber 41 are automatically performed as a consequence of the user rotating the removable cap 60 to remove it.

Penetrating the Distal End 27 of the Needle Cannula 25 Through the Septum 22.

Figure 8:
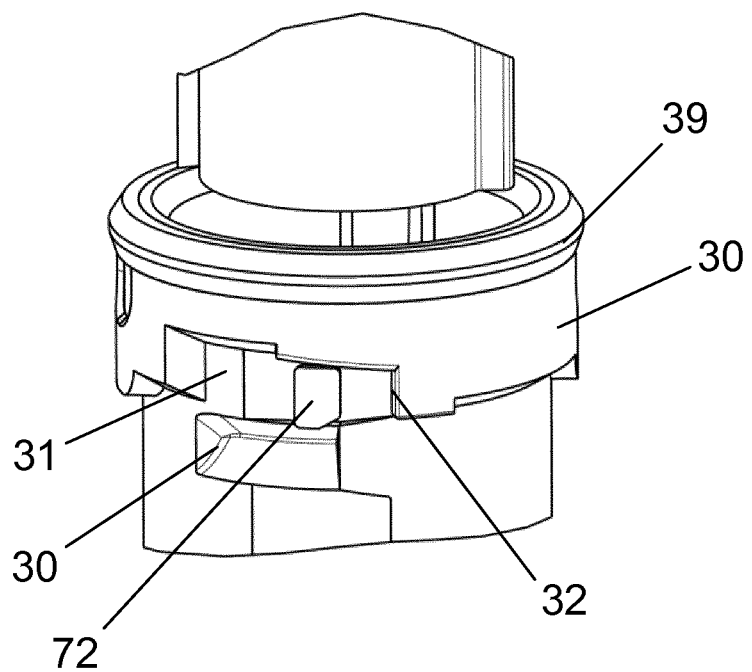
FIG. 8 show a detail of the engagement between the axially movable shield and the needle hub.

In order to perform an injection, the user needs to remove the removable cover 60. First time this is done an initiation process is automatically being carried out. When the user first rotates the removable cap 60, the longitudinal rib 65 abuts and transforms rotation to the axially movable shield 70 as disclosed in FIG. 5. During rotation of the axially movable shield 70, the second protrusion 72 rotates in a radial track 31 provided in the needle hub 30 as disclosed in FIG. 8. When the second protrusion 72 has moved to the end of the track 31, the second protrusion 72 abuts the end surface 32 of the radial track 31 and further rotation of the axially movable shield 70 is transformed to a rotation of the needle hub 30.

In an alternative embodiment, the first sterility barrier 39 can be made such that it transfers rotation from the axially movable shield 70 to the needle hub 30. This is preferably done by having sufficient friction between the radial outer surface of the first sterility barrier 39 and the inner surface of the axially movable shield 70.

Figure 9:
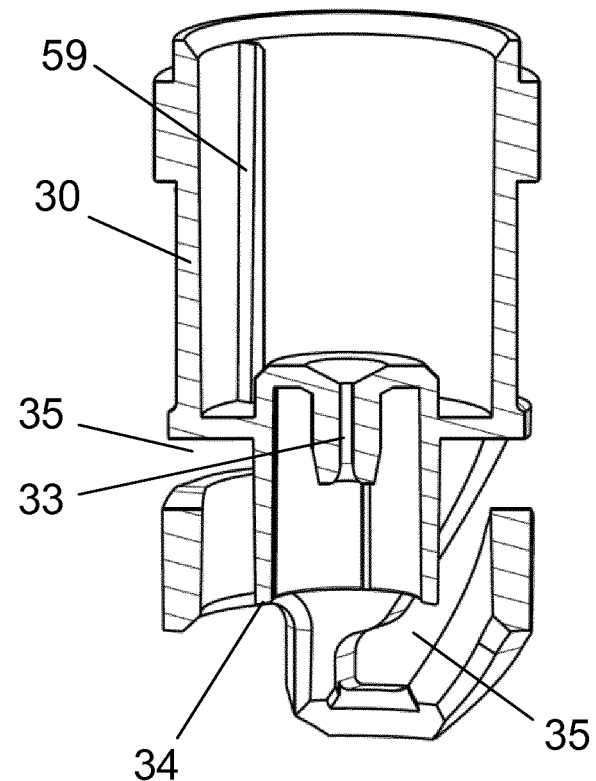
FIG. 9 show a cross sectional view of the needle hub.

The needle hub 30 is shown in a cross sectional view in FIG. 9 (without the first sterility barrier 39). Internally the needle hub 30 is provided with an axial opening 33 for securing the needle cannula 25 preferably by gluing. The axial opening 33 is surrounded by a flange which proximally terminates in an inner edge 34. Further, the outer surface of the needle hub 30 is provided with a helical track 35 which helical track 35 is engaged by a protrusion 12 provided on the cartridge holder 10 (see e.g. FIG. 2). As seen in FIG. 9, two such helical tracks 35 are provided in the disclosed embodiment.

Figure 10:
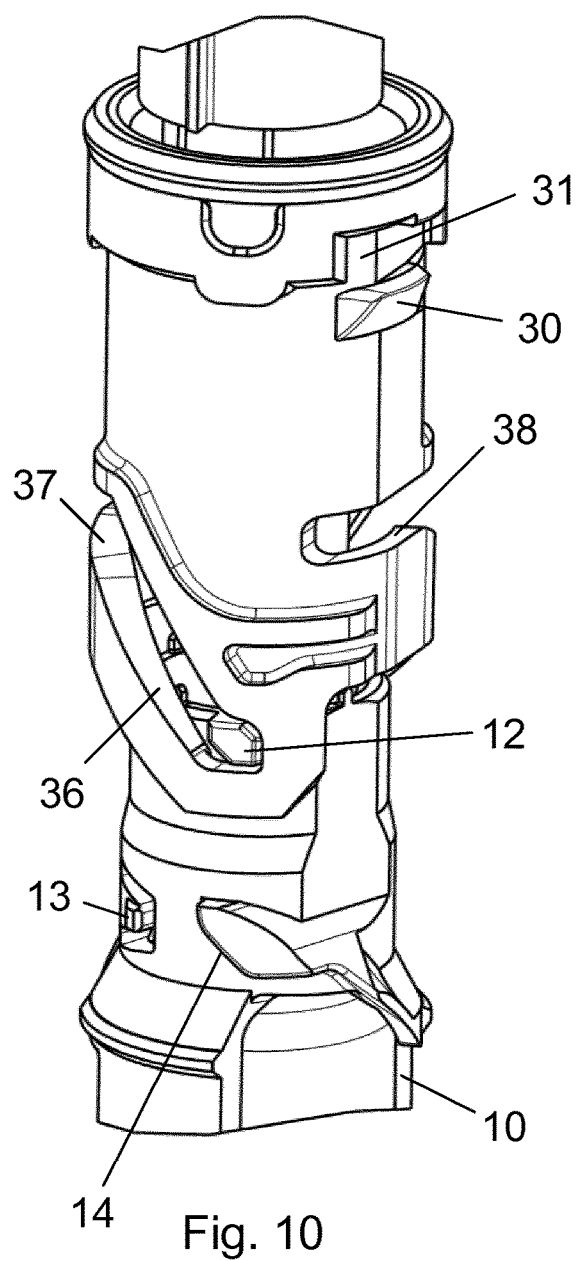
FIG. 10 show a detail of the engagement between the cartridge holder and the needle hub prior to the initiation process.
Figure 11:
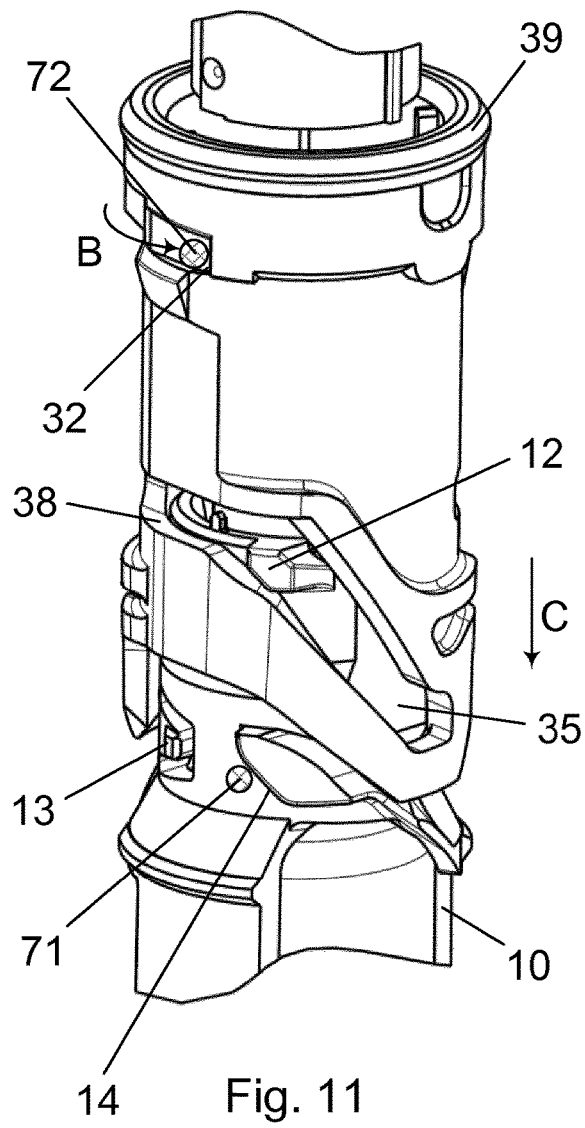
FIG. 11 show a detail of the engagement between the cartridge holder and the needle hub during proximal movement of the needle hub.
Figure 13:
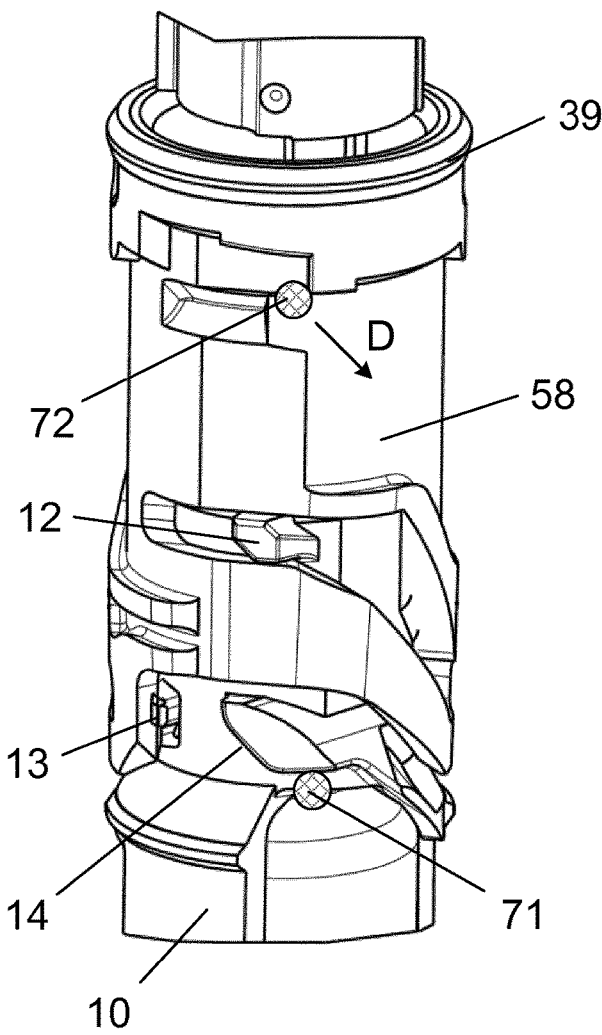
FIG. 13 show a detail of the engagement between the cartridge holder and the needle hub during filling of the cleaning chamber.

The engagement between the helical track 35 of the needle hub 30 and the protrusion 12 on the cartridge holder 10 is further disclosed in FIG. 10, FIG. 11 and FIG. 13.

FIG. 10 discloses the position in which the proximal end 27 of the needle cannula 25 is located distal to the septum 22 of the cartridge 20 which is the position disclosed in FIG. 1. The injection device is delivered to the user in this state and when the needle hub 30 is rotated by the engagement of the second protrusion 72 with the end surface 32 of the radial track 31, the needle hub 30 rotates with the axially movable shield 70 and moves in the proximal direction due to the helical inclination of the helical track 35. The rotational pressure applied to the needle hub 30 by the engagement of the second protrusion 72 of the axially movable shield 70 with the end surface 32 of the radial track 31 on the needle hub 30 is indicated with the arrow "B" in FIG. 11. However, the rotational force can alternatively be transferred via the friction between the first sterility barrier 39 and the axially movable shield 70.

The helical track 35 on the needle hub 30 comprises of three sections, a first helical section 36, a radial section 38 and an intermediate section 37 located there between. In FIG. 10 the protrusion 12 is located in the start position in the bottom of the first helical part 36 of the helical track 35. When the user rotate the needle hub 30 via the removable cap 60, the needle hub 30 travels in the proximal direction as indicated by the arrow "C" in FIG. 11 and after some degrees of rotation, the protrusion 12 enters into the intermediate part 37 of the helical track 35.

In order to enhance the understanding, the positions of the first protrusion 71 and the second protrusion 72 both located on the inner surface of the axially movable shield 70 is indicated in FIG. 11 and in FIG. 13.

In the position indicated in FIG. 11, the first protrusion 71 abuts the helical guiding flange 14 provided on the cartridge holder 10. At the same time the second protrusion 72 is moved to a position in the radial track 31 where the second protrusion 72 is allowed to move axially out of the radial track 31. This is due to the radial track 31 having an axial opening at the end of the radial track 31.

Figure 12:
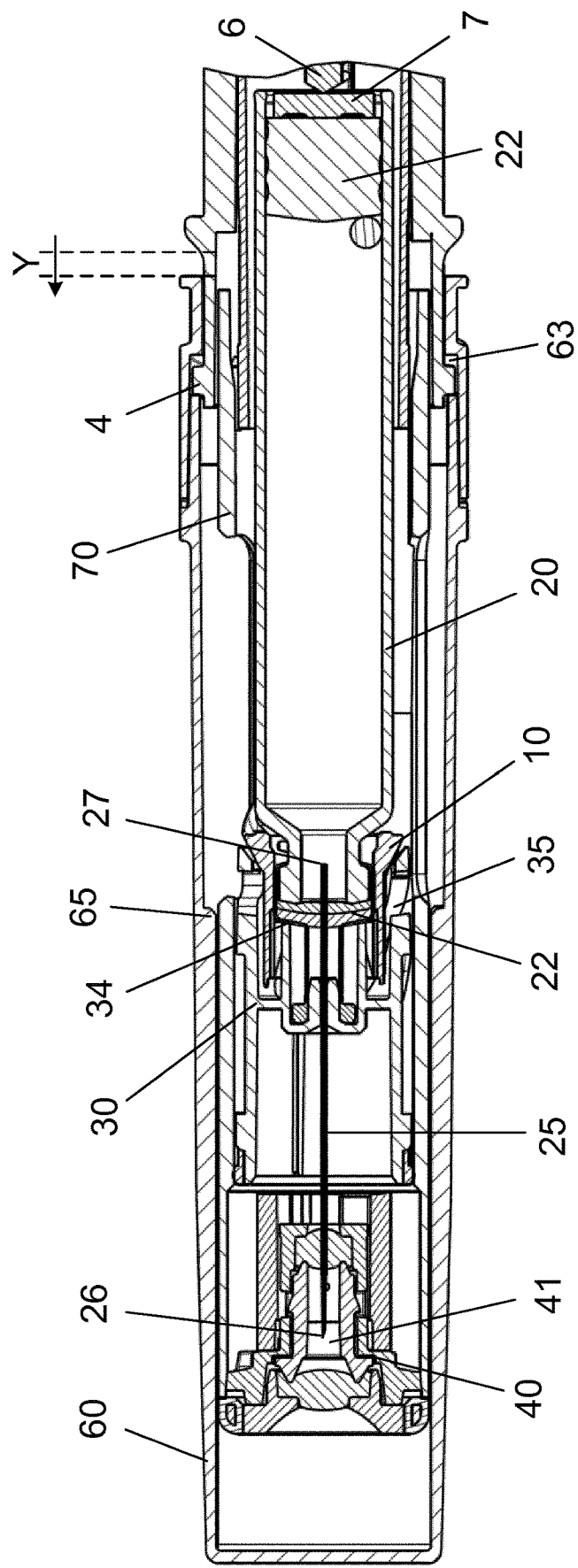
FIG. 12 show a cross sectional view of the front end of the injection device with the proximal end of the needle cannula penetrated into the cartridge.

In the position of FIG. 11, the proximal part 27 of the needle cannula 25 has penetrated through the septum 22 and the needle cannula 25 is now fully inserted into the cartridge 20 as disclosed in FIG. 12.

In FIG. 12, the removable cap 60 has moved a distance in the distal direction as the protrusion 4 on the housing base 1 has travelled helically in the helical cap track 63 inside the removable cap 60. The movement of the removable cap 60 as compared to FIG. 1 is indicated by the space "Y" in FIG. 12. At the same time the needle hub 30 has moved in the proximal direction due to engagement between the protrusion 12 and the helical track 35. As the needle hub 30 moves proximally it brings the axially movable shield 70 along since the second protrusion 72 is located in the radial track 31 and forced to move proximally together with the needle hub 30. As a result of this the axially movable shield 70 carrying the cleaning unit 40 and thus the cleaning chamber 41 moves proximally with the same speed as the needle hub 30 and the needle cannula 25 such that the distal tip 26 of the needle cannula 25 maintain its relative position inside the cleaning chamber 41 as depicted in FIG. 12.

Also in the position disclosed in FIG. 11 and in FIG. 12, the inner edge 34 of the needle hub 30 abuts the distal end of the cartridge 20.

The injection mechanism which is not shown in the figures has a threaded piston rod 6 for moving the plunger 21 in the distal direction. A piston rod foot 7 is provided between the piston rod 6 and the plunger 21 to distribute the force from the piston rod onto a larger area of the plunger 21. Since the injection device is a so-called pre-filled injection device, the piston rod 6 is secured to only move in the distal direction.

Filing of the Cleaning Chamber 41.

Figure 14:
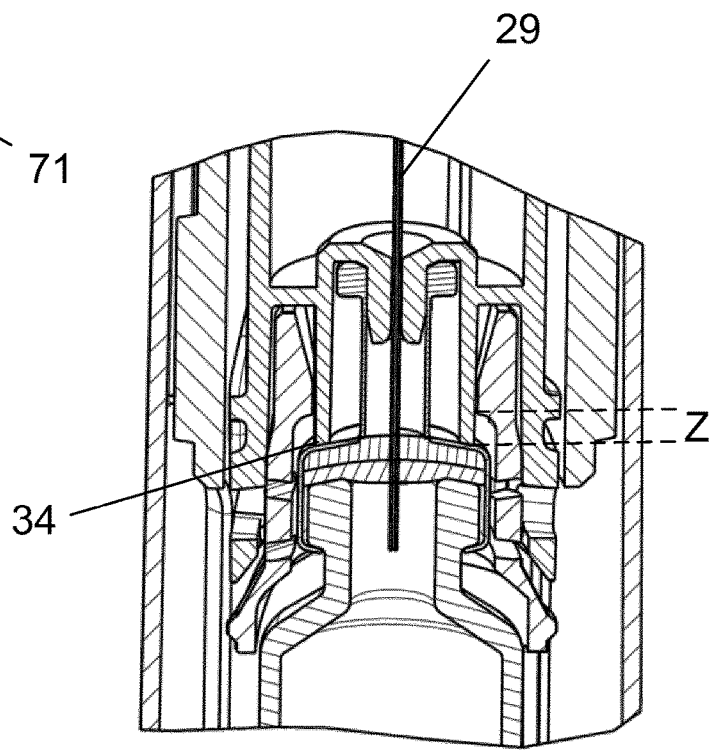
FIG. 14 show details of the abutment of the needle hub with the cartridge during filling of the cleaning chamber.

As the user keeps rotating the rotatable cap 60, the protrusion 12 is moved through the intermediate section 37 of the helical track 35 on the needle hub 30, relatively, as the rotating part is the needle hub 30. Since the slope is somewhat smaller than the slope of the first helical section 36 of the helical track 35, a larger force can be transmitted. This force is via the inner edge 34 of the needle hub 30 transmitted to a movement of the cartridge 20 as indicated by the distance "Z" in FIG. 14 and FIG. 15.

Since the piston rod foot 7 and thus the plunger 21 is maintained in a stationary position such proximal movement of the cartridge 20 builds up pressure inside the cartridge 20. This pressure forces a quantum of the liquid inside the cartridge 20 to flow through the lumen 29 of the needle cannula 25 and into the cleaning chamber 41 which is thus being filled with liquid drug.

Figure 15:
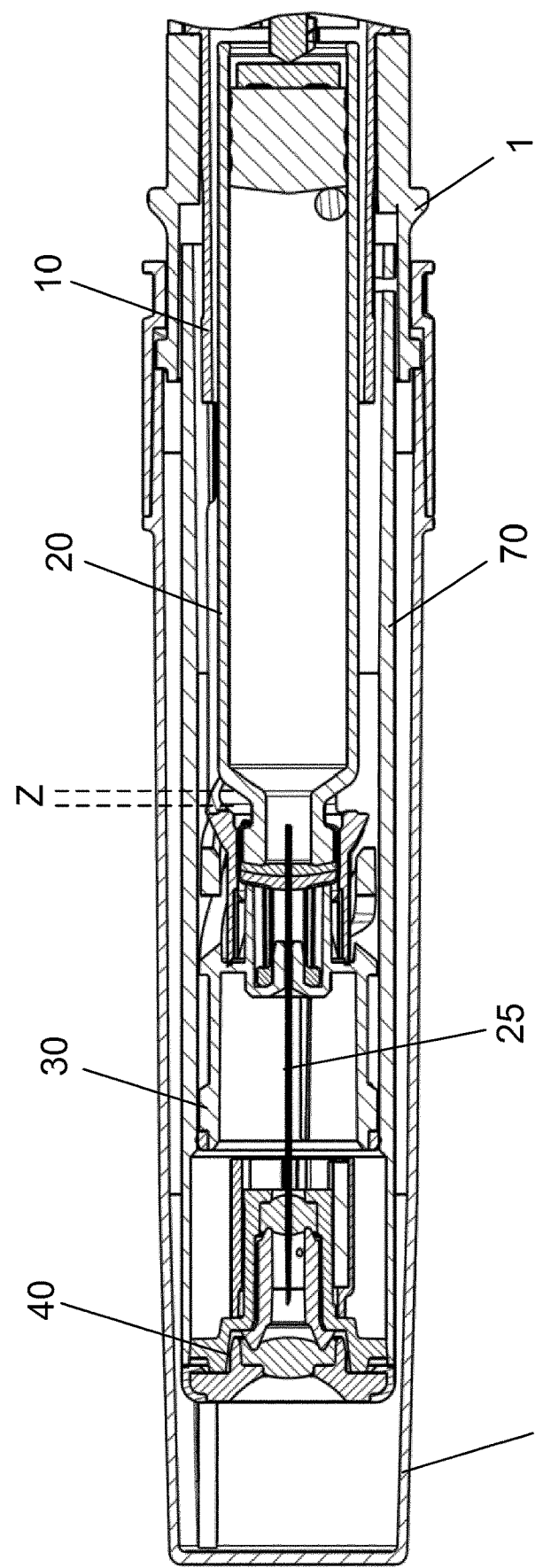
FIG. 15 show a cross sectional view of the front end of the injection device during filling of the cleaning chamber.

The state in which the cleaning chamber 41 is filled is disclosed in FIG. 13 and FIG. 15. After having passed through the intermediate section 37, the protrusion 12 is now (relatively) located in the radial section 38 of the track 35 and the cleaning chamber 41 is slowly being filled with liquid drug from the cartridge 20 as the liquid drug flows through the lumen 29 of the needle cannula 25.

Initiated and Locked.

Figure 16:
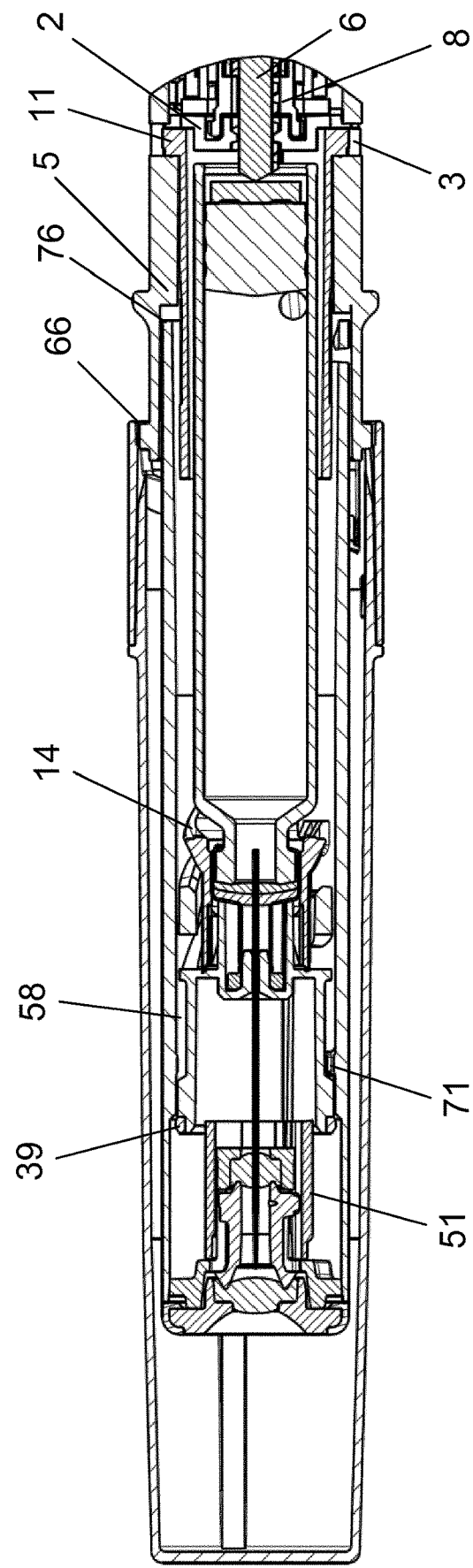
FIG. 16 show a cross sectional view of the front end of the injection device with the axially movable shield positioned in the locked position.

When the user rotates the removable cap 60 to its end destination disclosed in FIG. 16, the removable cap 60 can be axially removed from the housing base 1 i.e. the protrusion 4 can escape out of the helical cap track 63 via the track opening 66. In this position, the needle hub 30 automatically locks to the cartridge holder 10 by the flexible locking arm 13 provided on the cartridge holder 10 engaging the bottom of the helical track 35. For this purpose two such helical tracks 35 are provided together with two flexible locking arms 35 in a 180 degrees separation.

Further, when the protrusion 12 is moved radially into the radial section 38 of the helical track 35 as shown in FIG. 13, the first protrusion 71 slides along the slope of the helical flange 14 as also indicated in FIG. 13. Since the first protrusion 71 is provided on the axially movable shield 70 and the needle hub 30 in this position is fixed, the axially movable shield 70 is pulled in the proximal direction by the helical flange 14. This movement of the axially movable shield 70 in the proximal direction also moves the second protrusion 72 into an open area 58 on the needle hub 30 as indicated by the arrow "D". Inside this area 58, the second protrusion 72 is free to move axially.

The proximal movement of the axially movable shield 70 also brings the first sterility barrier 39 out of contact with the axially movable shield 70 as best seen in FIG. 16 such that further movements of the axially movable shield 70 can be performed with less friction.

However, in the position depicted in FIG. 16, the axially movable shield 70 is unable to move axially since the proximal end 76 of the axially movable shield 70 abuts the internal rib 5 inside the housing base 1. This is further disclosed in FIG. 19 in which a part of the housing base 1 has been cut a away to allow a view of the internal rib 5 provided on the inside of the housing base 1 as seen in FIG. 3.

Once the removable cap 60 has been rotated to its end position disclosed in FIG. 16, the user axially removes the removable cap 60.

Unlocking

Figure 19:
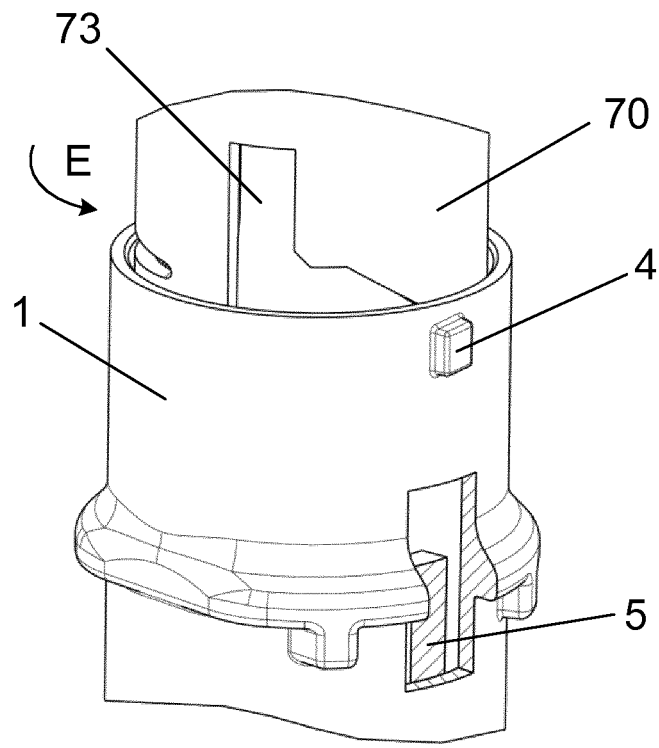
FIG. 19 show a detail of the interface between the housing assembly and the axially movable shield.

When the user manually rotates the axially movable shield 70 in an anti-clockwise direction as indicated by the arrow "E" in FIG. 19, the longitudinal slit 73 can be brought into alignment with the internal rib 5 inside the housing base 1 to allow axial movement of the axially movable shield 70.

As the user rotate the axially movable shield 70 to such alignment (slit 73 with internal rib 5), the second protrusion 72 moves down the helical flange 14 to a position indicated in FIG. 2 in which the first protrusion 71 is located in a longitudinal track 15 provided in the cartridge holder 10 thus allowing the first protrusion 71 to move axially in this longitudinal track 15. In this position, the axially movable shield 70 has moved axially due to the engagement between the first protrusion 71 and the helical flange 14 such that the distal tip 26 of the needle cannula 25 has penetrated through the distal septum 43 of the cleaning unit 40 as depicted in FIG. 17.

Once the axially movable shield 70 has been rotated to its unlocked position, the longitudinal window 74 of the axially movable shield 70 has also been rotated into alignment with the cartridge holder window 16 such that the user can now view the content of cartridge 20. The alignment of the two windows 74, 16 is further a visual indication to the user that the injection device is now unlocked and ready to perform an injection.

Figure 17:
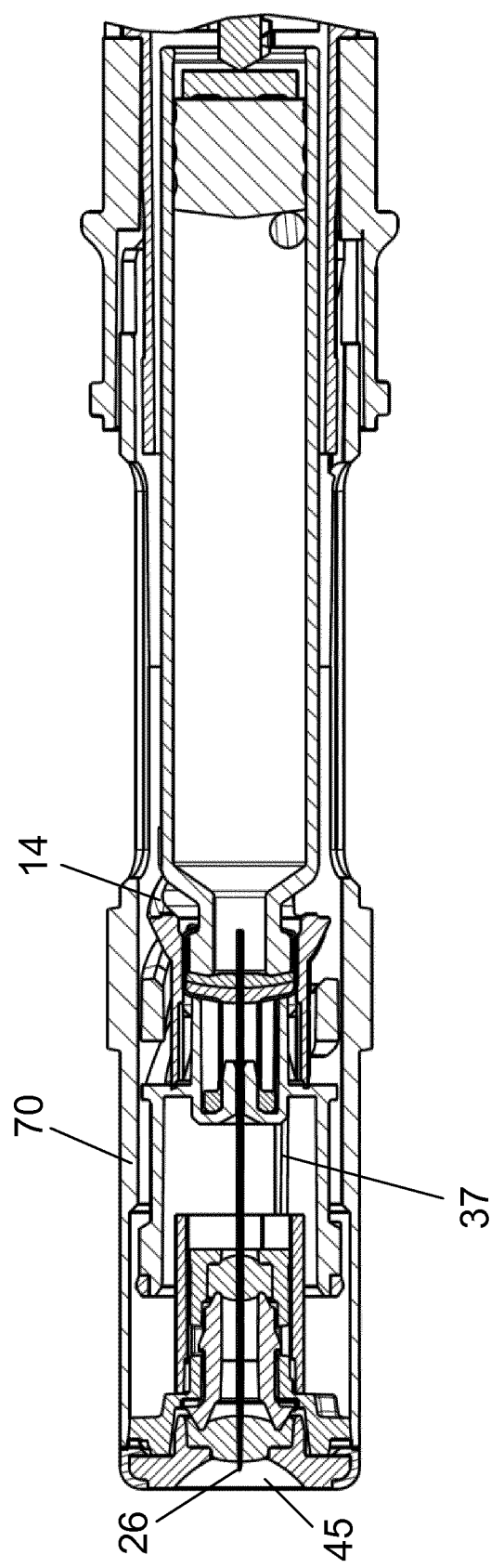
FIG. 17 show a cross sectional view of the front end of the injection device in the unlocked position ready to dose.

In this ready-to-inject position as disclosed in FIG. 17, the distal tip 26 of the needle cannula 25 is positioned in a concave portion 45 provided in the cleaning unit 40 such that the user can press the distal surface of the cleaning unit 40 against the skin.

Figure 20:
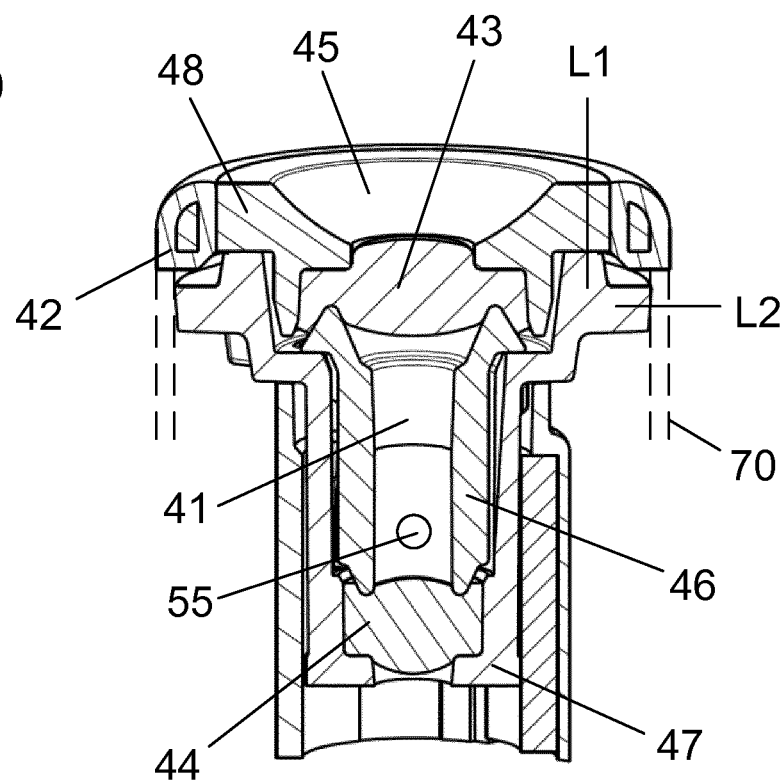
FIG. 20 show a cross sectional view of the cleaning module.

As best seen in FIG. 20, the cleaning unit 40 comprises the cleaning chamber 41 which distally is sealed by a distal septum 43 and proximally by a proximal septum 44. The distal septum 43 is self-sealing to allow the needle cannula 25 to pass through the distal septum 43 multiple times. However, the proximal septum 44 could alternatively be formed as a seal just sealing around the outer surface of the needle cannula 25 as the distal tip 26 of needle cannula 25 does not repeatedly pass through this proximal septum 44. The two septum 43, 44 are kept apart by an intermediate member 46 and the cleaning unit 40 is welded together by welding an outer part 47 to a top part 48. The welding used is preferably a laser welding along the line L1.

The cleaning unit 40 is further welded to the axially movable shield 70 (indicated by broken lines in FIG. 20) such that the cleaning unit 40 operates as a part of the axially movable shield 70. The welding between the cleaning unit 40 and the axially movable shield 70 is also made as a laser welding preferably along the line L2. Most distally the cleaning unit 40 connects to the second sterility barrier 42 which also connects to the axially movable shield 70. The second sterility barrier 42 is preferably moulded to the cleaning unit 40 e.g. in a 2K moulding.

During sterilisation and during assembly, the axially movable shield 70 with the cleaning unit 40 welded thereto and the needle hub 30 mounted inside the axially movable shield 70 can be handled as one component.

Figure 21:
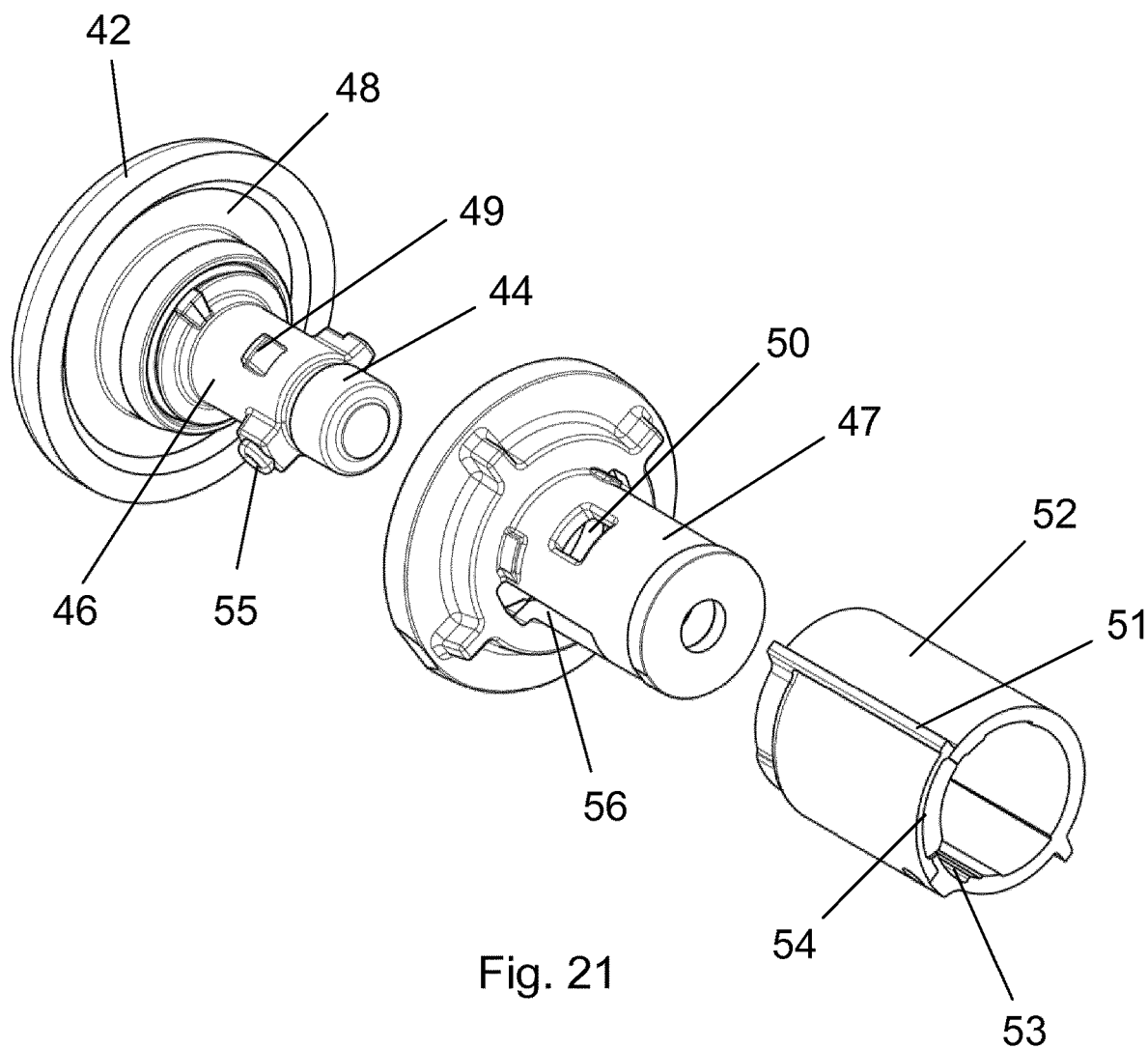
FIG. 21 show a partly exploded view of the cleaning module with the valve.

The cleaning unit 40 is disclosed in a somewhat exploded view in FIG. 21. As can be seen the intermediate part 46 is on an external surface provided with a click protrusion 49 which engages an opening 50 provided in the outer part 47 such that the cleaning unit 40 can be pre-assembled before the weldings are performed along the lines L1 and L2.

The second sterility barrier 42 is preferably formed together with the top part 48 in a 2K moulding. The second sterility barrier 42 can also be moulded to the axially movable shield 70. Both the first sterility barrier 39 and the second sterility barrier 42 are preferably made from a Thermo Plastic Elastomer (TPE) in a 2K moulding.

Proximally FIG. 16 discloses the piston rod 6. This piston rod 6 is threaded on the outside such that it is rotated forward in the threaded nut member 2 whenever the piston rod 6 is rotated. In order to rotate the piston rod 6, a piston rod guide 8 is provided which engages a longitudinal groove provided in the piston rod 6. This piston rod guide 8 is rotated by a well-known torsion spring engine e.g. as disclosed in European Patent Application EP16163893.7 during expelling of a set dose. Further, such piston rod guide 8 is designed such that it can only rotate in a dose expelling direction thus preventing the piston rod 6 from moving in the proximal direction. As disclosed in European Patent Application EP16163893.7 such torsion spring engine is released by proximal movement of the axially movable shield 70.

Valve

As best seen in FIG. 9, the needle hub 30 is on the outer surface provided with a needle hub rib 59 which engages a similar valve rib 51 provided externally on the valve 52 seen in FIG. 21.

In FIG. 16, the needle hub 30 is locked to the cartridge holder 10 by the flexible arms 13 engaging the track 35 as explained. When the user rotates the axially movable shield 70 to unlock the injection device the cleaning unit 40 rotates with the axially movable shield 70 as the cleaning unit 40 is welded to the axially movable shield 70.

On the outer surface of the outer part 47 a valve 52 is positioned. As disclosed in FIG. 21, this valve has an inner groove 53 and an inner sealing 54 preferably also made form a TPE in a 2K moulding.

During filling of the cleaning chamber 41, the longitudinal groove 52 is positioned over an opening 55 in the intermediate part 46. This opening 55 connects to the interior of the cleaning chamber 41. Due to this opening 55 air and liquid can escape from the cleaning chamber 41 as the cleaning chamber 41 is being filled with liquid drug from the cartridge 20.

As can be seen from FIG. 21, the opening 55 is carried on an extension which slides into an open recess 56 in the outer part 47 during assembly.

Once the cleaning chamber 41 is filled and the user rotates the axially movable shield 70 for the first time the cleaning unit 40 rotates together with the axially movable shield 70, however the valve 50 remains in its position since the abutment between the needle hub rib 59 and the valve rib 51 prevents rotation of the valve 52.

As the cleaning unit 40 rotates, the opening 55 is rotated to the area of the valve 52 carrying the inner sealing 54 which henceforth prevents further air and drug to flow out from the cleaning chamber 41.

Next time the user rotates the axially movable shield 70 back to the closed position, the valve 52 will remain in its relative position on the cleaning unit 40 and rotate together with the cleaning unit 40. In order to make this happen friction or click means can be provided between the outer surface of the cleaning unit 40 and the valve 52.

The shut-off function of the valve 52 therefore only works the first time the axially movable shield 70 and thus the cleaning unit 40 is rotated.

Injection

Figure 18:
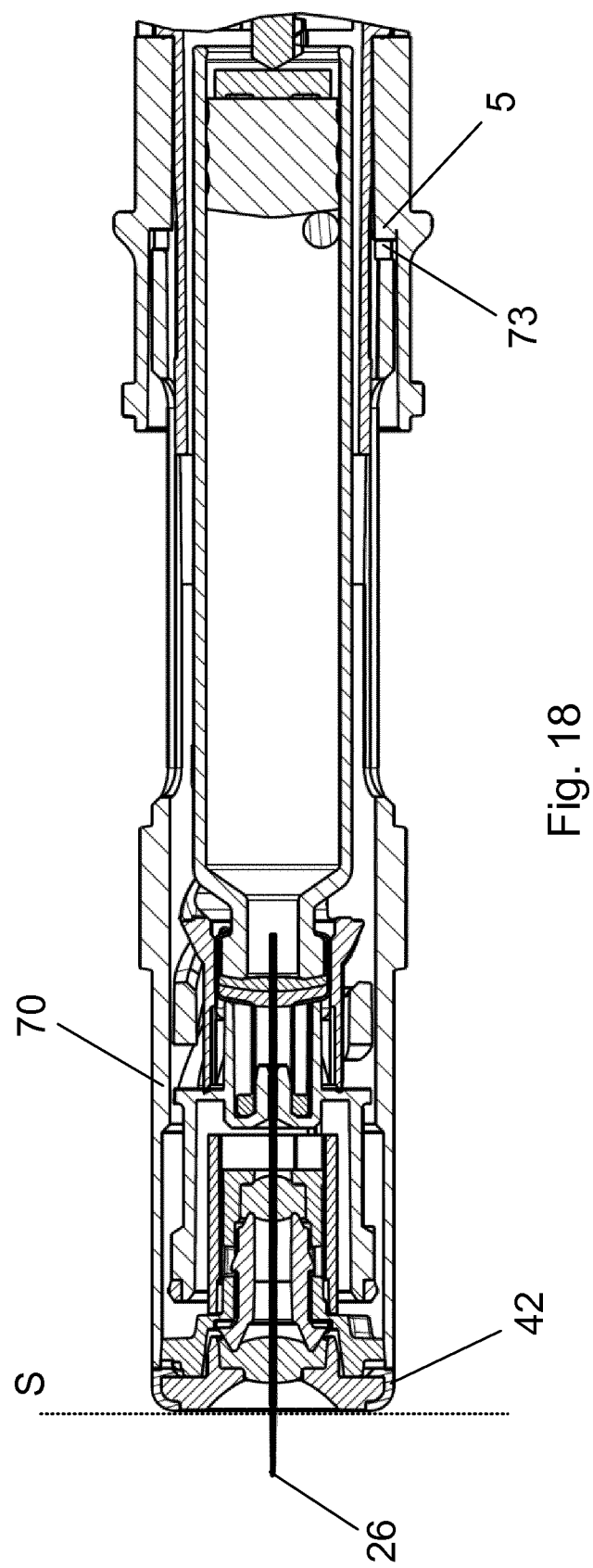
FIG. 18 show a cross sectional view of the front end of the injection device during dosing.

In order to perform an injection, the user pushes the distal end of the axially movable shield 70 against the skin "S" as disclosed in FIG. 18. When the axially movable shield 70 is moved proximally as the distal tip 26 of the needle cannula 25 moves deeper into the skin "S", the torsion spring engine is released to expel the set dose through the lumen 29 of the needle cannula 25 and into the body of the user.

As further seen in FIG. 18, the second sterility barrier 42 is rounded at the distal end of the cleaning unit 40 such that the sterility barrier 42 abut the skin "S" during injection. Since the second sterility barrier 42 is made from a TPE material this prevents the cleaning unit 40 and thus the axially movable shield 70 form sliding vertically on the surface of the skin "S".

Once the injection is finished, the user removes the axially movable shield 70 carrying the cleaning unit 40 from the skin "S" where after a not-shown compression spring moves the axially movable shield 70 back to the position disclosed in FIG. 17 i.e. the position in which the first protrusion 71 is positioned distally in the longitudinal track 15 on the cartridge holder 10 as best seen in FIG. 2.

From this position, the user by rotating the axially movable shield 70 brings the axially movable shield 70 into the position disclosed in FIG. 16 where after the removable cap 60 can be mounted. As the user rotate the axially movable shield 70 back to the position disclosed in FIG. 16, the first protrusion 71 slides back on the flange 14 to the position disclosed in FIG. 13 and from which position the user can again unlock the axially movable shield 70 by performing a new rotation.

Second Embodiment

FIGS. 22 to 35 discloses a slightly different embodiment in which similar elements are numbered by the same the same reference number however with a "1" in front of the number.

In this embodiment, the needle hub 130 is shaped as a longitudinal tube structure surrounding the cartridge 120 and an initiator 180 has been inserted in the housing 101 as will be explained.

Figure 22:
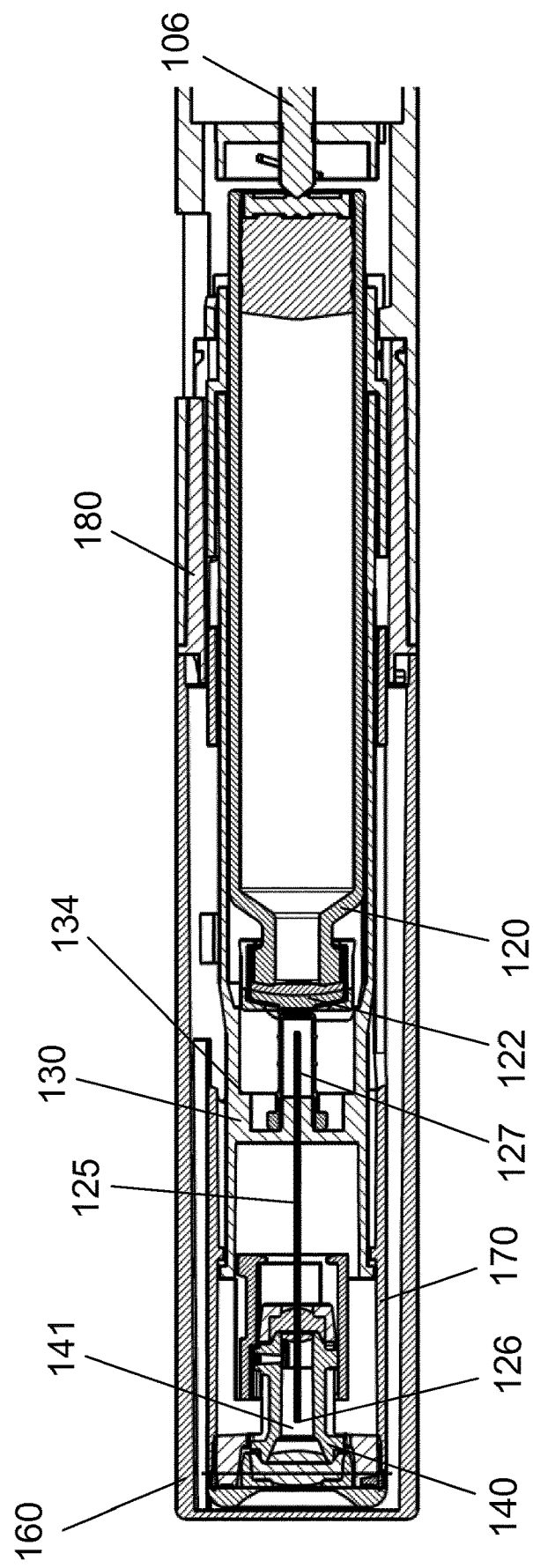
FIG. 22 show a cross sectional view of the front end of the injection device before the initiation process is started according to a second embodiment of the invention.

As in the previous embodiment, the needle hub 130 is attached to the needle cannula 125 which in the storage stage depicted in FIG. 22 is decoupled from the cartridge 120 such that the proximal end 127 of the needle cannula 120 is located distal to the septum 122 of the cartridge 120.

The distal part of the injection device is in the storage stage covered by a removable cap 160 and the axially movable shield 170 distally carries the cleaning module 140.

Figure 23:
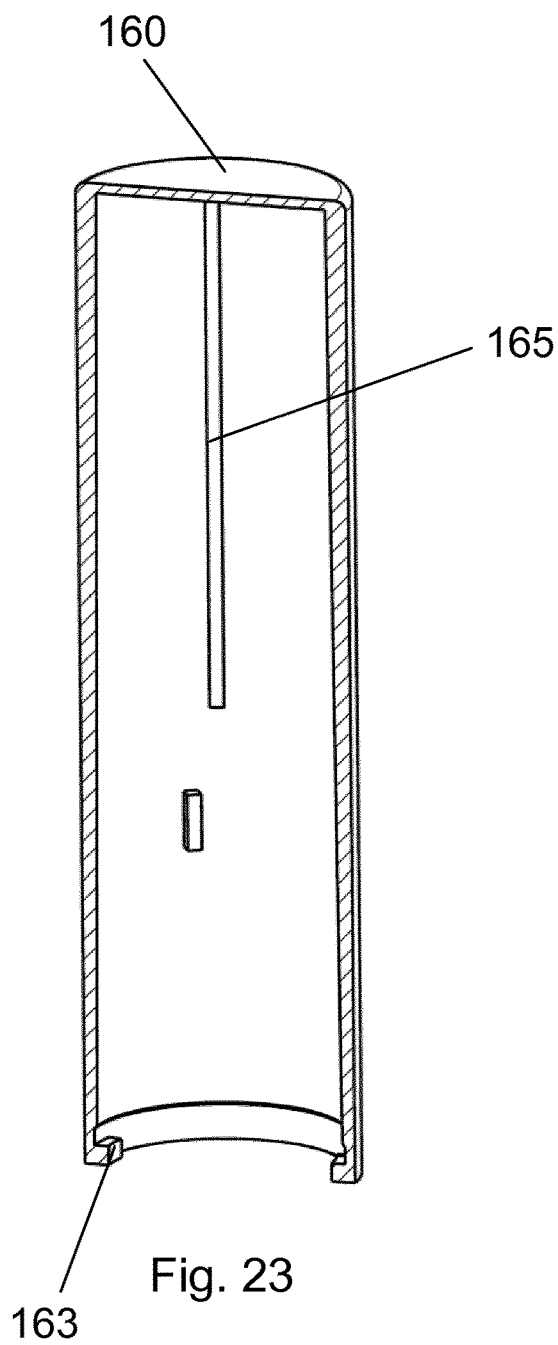
FIG. 23 show a cross sectional view of the removable cap according to the second embodiment FIG. 24 show a perspective view of the housing structure according to the second embodiment of the invention.
Figure 24:
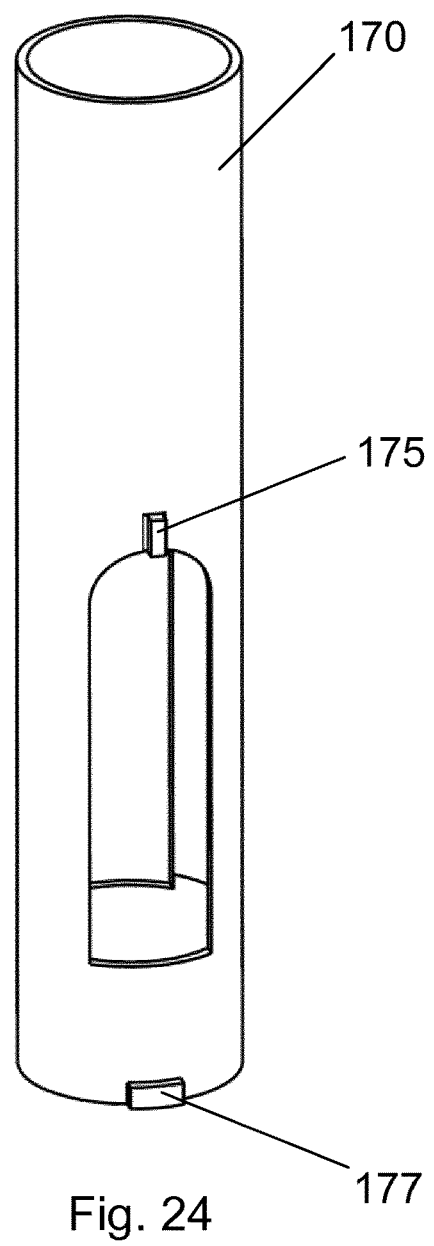
Figure 25:
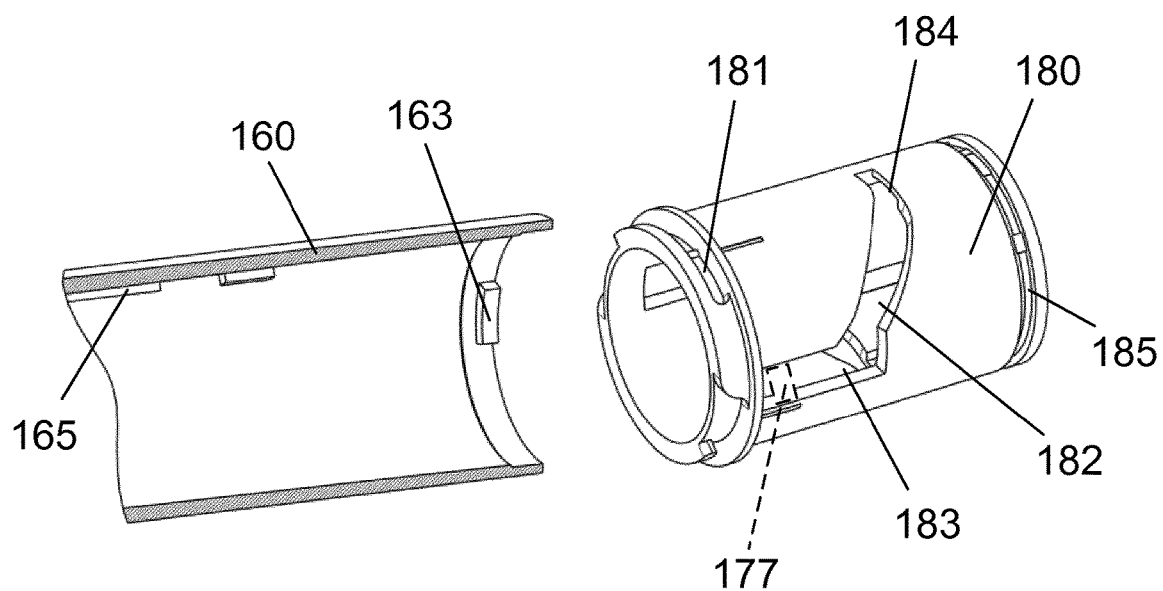
FIG. 25 show a perspective view of the engagement between the removable cap and the initiator according to the second embodiment of the invention.

As in the first embodiment, the removable cap 160 is on the inside provided with a longitudinal rib 165 as disclosed in FIG. 23. This longitudinal rib 165 engages an outwardly pointing rib 175 provided externally on the axially movable shield 170 as disclosed in FIG. 24. Further, the removable cap 160 is provided with an inwardly pointing protrusion 163 which is engaged in a guiding track 181 provided on the initiator 180 which is best seen in FIG. 25. As a consequence of this engagement, the user is forced to rotate the removable cap 160 out of the track 181 before the removable cap 160 can be axially removed.

The axially movable shield 170 is distally provided with the cleaning module 140 which can be a module like the one disclosed in the first embodiment (FIG. 20). The cleaning module 140 has a cleaning chamber 141 in which the distal tip 126 of the needle cannula 120 is maintained between injections. Proximally the axially movable shield 170 is provided with a knob 177, the function of which will be explained.

The initiator 180 which is disclosed in details in FIG. 25 is provided with a ring-shaped groove 185 which is secured to the housing 101 via the flexible holder 103 such that the initiator 180 can only rotate relatively to the housing 101 but not axially. The initiator 180 is further provided with a helical track 182 which is broken through the surface structure. This helical track 182 connects to two axial tracks 183, 184. On the inner surface the initiator 180 is further provided with a longitudinal track 186 which engages an outwardly pointing protrusion 132 provided on the outer surface of the needle hub 130.

Figure 27:
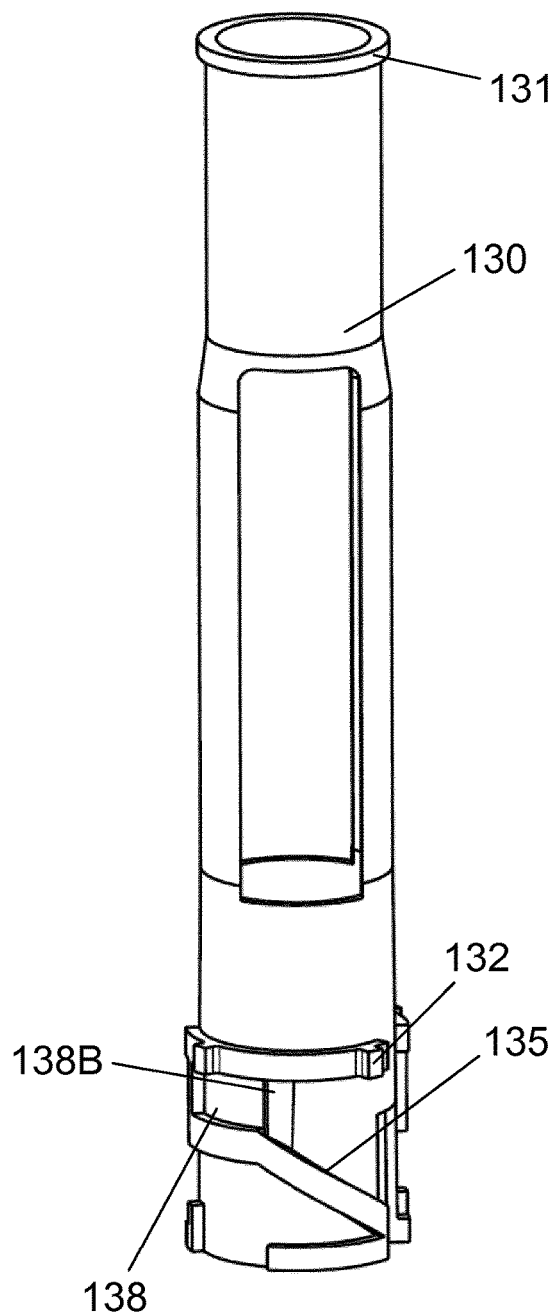
FIG. 27 show a perspective view of the needle hub according to the second embodiment of the invention.

The needle hub 130 disclosed in FIG. 27 is rotatably mounted in the housing 101 and provided with a helical ramp 135 the purpose of which will be explained in the following. The distal end of the needle hub 130 is shaped into a radial flange 131 and the outer surface carries the protrusions 132.

Figure 28:
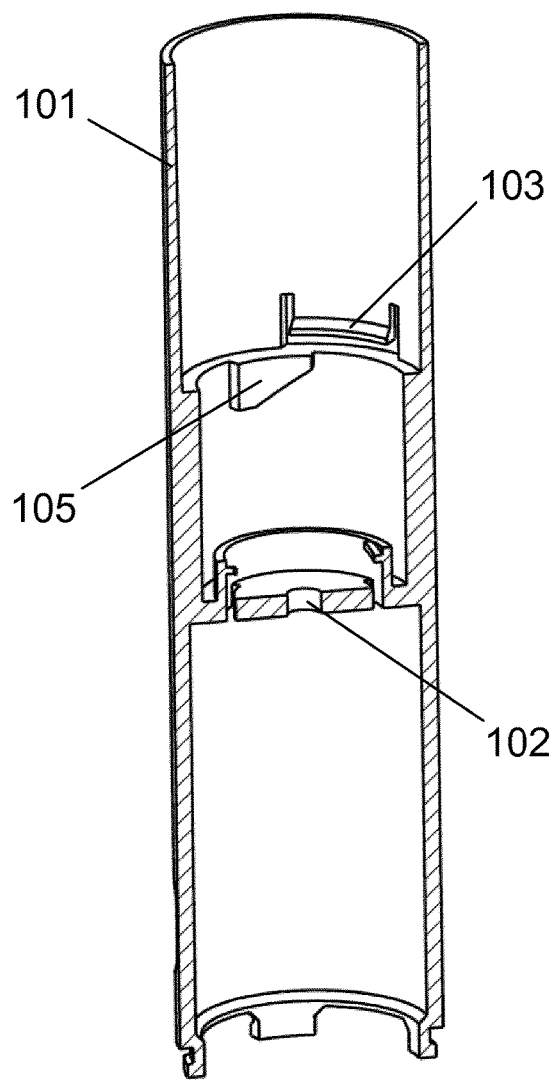
FIG. 28 show a cross sectional view of the housing base according to the second embodiment of the invention.

The housing 101 is disclosed in FIG. 28 and has internally a nut member 102 for guiding forward the piston rod 106. The inner surface of the housing 101 also carries the holder 103 for the initiator 180 and a guiding knop 105.

Although the different tracks and protrusions in the mechanism are referred to in singularity they can be provided in any number needed. It is particular noted that the various tracks 182, 183, 184, 186 in the initiator 180, the guiding knop 105 inside the housing 101, the helical ramp 135 on the needle hub 130 and the knop 177 on the axially movable shield 170 are provided in a pair of two.

The injection device is delivered to the user in the state depicted in FIG. 22. In this state the distal tip 126 of the needle cannula 120 is located inside the cleaning chamber 141 which is empty and the proximal part 127 of the needle cannula 120 is located distal to the septum 122 of the cartridge 120.

As in the first embodiment, the cleaning chamber 141 is empty and ready to receive to an amount of the preservative containing liquid drug contained in the cartridge 120 via an initiation procedure.

In order to prepare the injection device for injections, the user removes the removable cap 160 by rotating the removable cap 160 and henceforth the inwardly pointing protrusion 163 relatively to the guiding track 181 provided on the initiator 180.

The forced rotation of the removable cap 160 forces the axially movable shield 170 to rotate simultaneously with the removable cap 160 due to the engagement of the longitudinal rib 165 with the outwardly pointing rib 175 provided on the axially movable shield 170.

Figure 26:
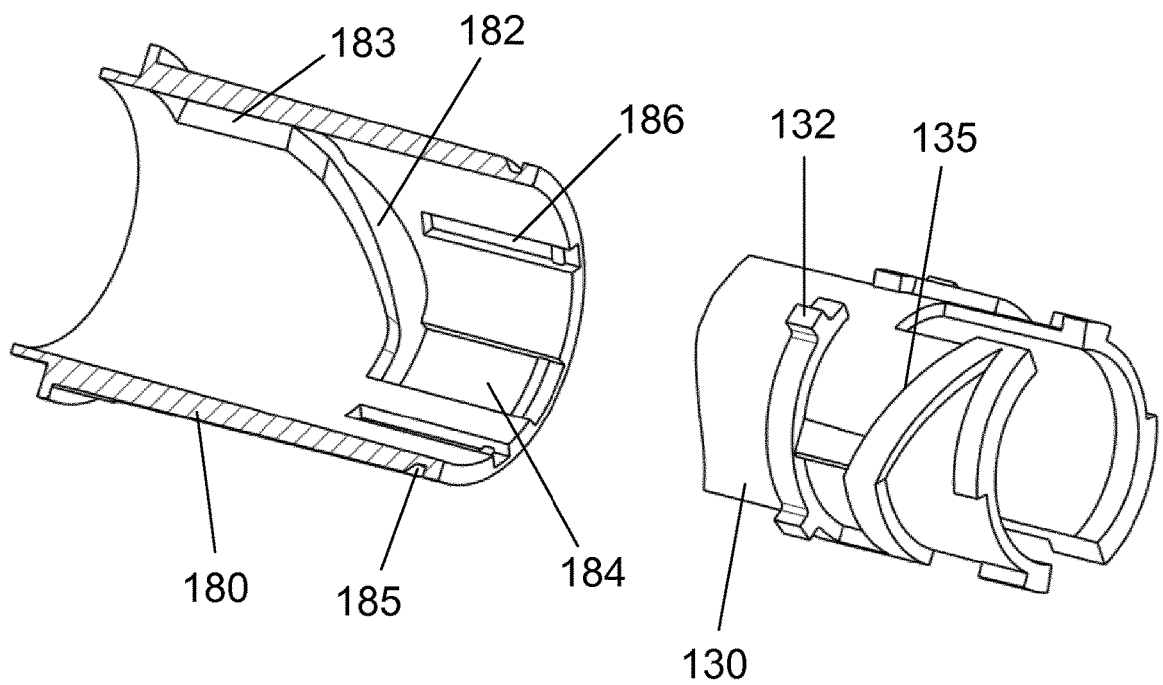
FIG. 26 show a perspective view of the engagement between the initiator and the needle hub according to the second embodiment of the invention.

The initiator 180 carrying the guiding track 181 has as disclosed in FIG. 25 a first axial track 183 which terminates into a helical track 182 which again leads to a second axial track 184 which is not broken through the surface as can be best seen in FIG. 26.

The knop 177 provided on the axially movable shield 170 is in this initial state located in the first axial track 183. The position of the knop 177 is indicated with broken lines in FIG. 25.

As the axially movable shield 170 is now rotated by the removable cap 160, the initiator 180 is forced to follow this rotation due to abutment of the knop 177 with the sidewall of the first axial track 183 in the initiator 180.

As best seen in FIG. 26, the longitudinal track 186 provided on the inner surface of the initiator 180 engage the outwardly pointing protrusion 132 on the needle hub 130. The rotation of the removable cap 160 is thus first transferred to a rotation of the axially movable shield 170 which again rotate the initiator 180 which transfers rotation to the needle hub 130.

Figure 29A:
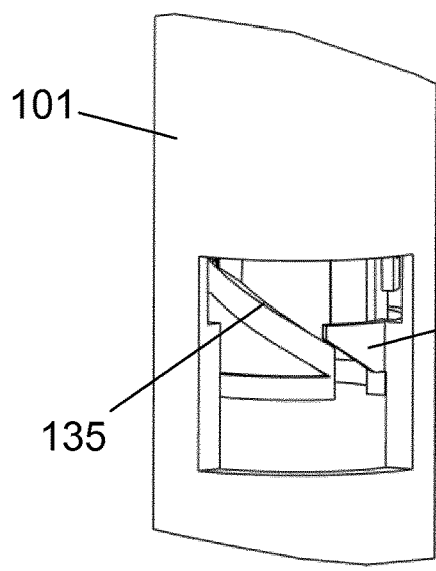
FIG. 29A-B show the engagement between the housing and the needle hub according to the second embodiment of the invention.
Figure 29B:
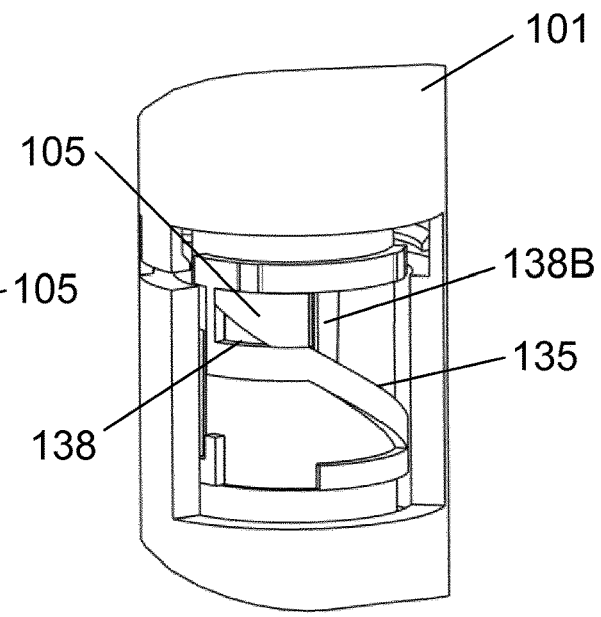

In the FIGS. 29A and 29B, the housing 101 has been cut open in order to view the engagement between the inner surface of the housing 101 and the needle hub 130.

In the initial position, the guiding knop 105 on the inner surface of the housing 101 is located at the lower end of the helical ramp 135 as disclosed in FIG. 29B. As the needle hub is rotated, the needle hub 130 is forced in the proximal direction due to the engagement between the helical ramp 135 and the guiding knop 105. The helical ramp 135 terminates in a radial track 138 into which the guiding knop 105 has moved in FIG. 29B. This radial track 138 is provided with an axial locking rib 138B which irreversible secures the guiding knop 105 to the needle hub 130.

In this position, the needle hub 130 is irreversible connected to the housing 101 such that the needle hub 130 and the housing 101 hereafter operate as one element.

Figure 32:
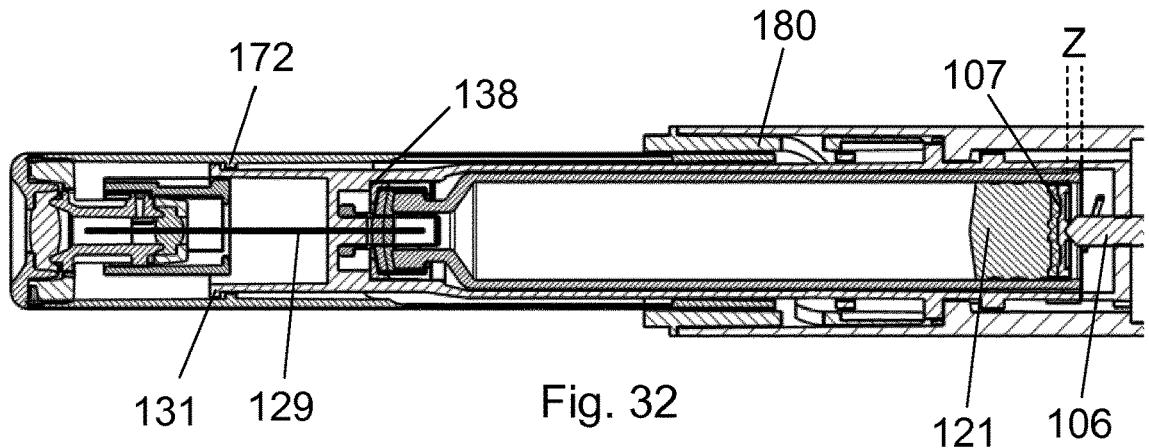
FIG. 32 show a cross sectional view of front end of the injection device during filling of the cleaning chamber according to the second embodiment of the invention.

In the position disclosed in FIG. 29B, the needle hub 130 has been moved from the initial position disclosed in FIG. 22 to the filling position disclosed in FIG. 32.

In the filling position disclosed in FIG. 32, the proximal part 127 of the needle cannula 120 has been penetrated through the septum 122 of the cartridge 120 and liquid communication has been established between the interior of the cartridge 120 and the cleaning chamber 141.

The axial movement of the needle hub 130 is such that the proximal part 127 of the needle cannula 120 is inserted into the cartridge 120 and the distance is further calculated such that the surface 138 inside the needle hub 130 abut the distal end of the cartridge 120 and moves the cartridge 120 a distance "Z" in the proximal direction. As the cartridge 120 is moved the distance "Z" as indicated in FIG. 32 and the piston rod 106, the piston rod foot 107 and the plunger 121 remains in a locked position a pressure will built up inside the cartridge 120.

As the needle hub 130 moves in the proximal direction it brings along the axially movable shield 170 as the distal flange 131 engages an inwardly pointing rib 172 provided on the inner surface of the axially movable shield 170.

Since the needle hub 170 which carries the needle cannula 120 and the axially movable shield 170 which carries the cleaning chamber 141 moves simultaneously, the distal tip 126 of the needle cannula 126 remains in its relative position inside the cleaning chamber 141 as the needle hub 170 and the needle shield travels proximally. At the same time as the axially movable shield 170 travels in the proximal direction so does the knop 177 as it is provided on the axially movable shield 170. Once the needle hub 130 is in the position disclosed in FIG. 29B, the knop 177 has moved axially down the first axial track 183 and is now positioned at the entrance to the helical track 182 as disclosed in FIG. 177.

This pressure built up inside the cartridge 120 will force a quantum of the preservative containing liquid drug through the lumen 129 of the needle cannula 120 and into the cleaning chamber 141.

In the filling position disclosed in FIG. 32, the initiator 180 is locked to the housing 101 as the guiding knop 105 in the housing 101 is irreversible locked in the radial track 138 of the initiator 180. This also secures the needle hub 130 to the housing 101. Further, in this position the cleaning chamber 141 is being filled with preservative containing drug from the cartridge 120.

Due to various tolerances a pressure larger than needed can be built up inside the cartridge 120. In order to equalize this pressure before performing an injection, the distal tip 126 of the needle cannula 120 has to be penetrated through the distal barrier 143 of the cleaning chamber 141.

Figure 30:
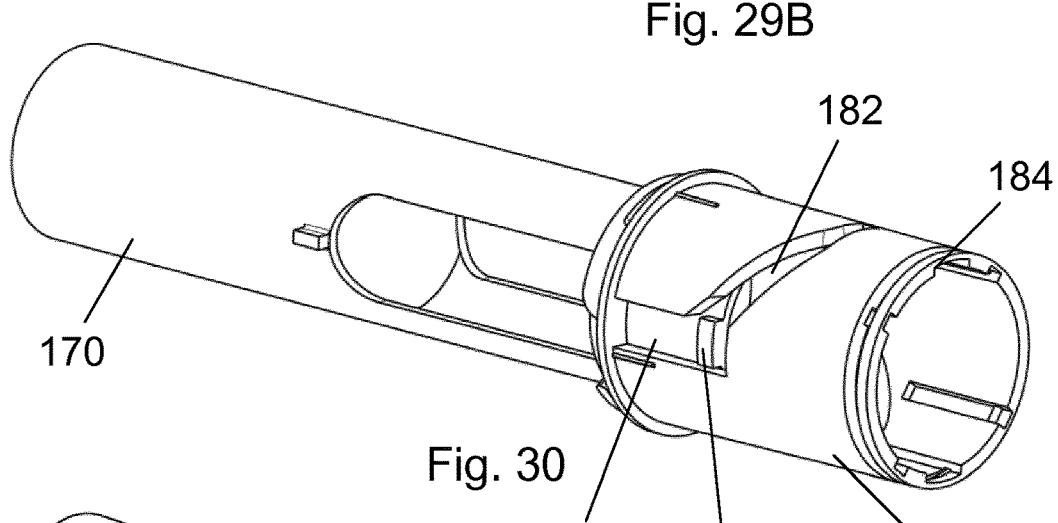
FIG. 30 show the engagement between the axially movable shield and the initiator after filling of the cleaning chamber according to the second embodiment of the invention.
Figure 31:
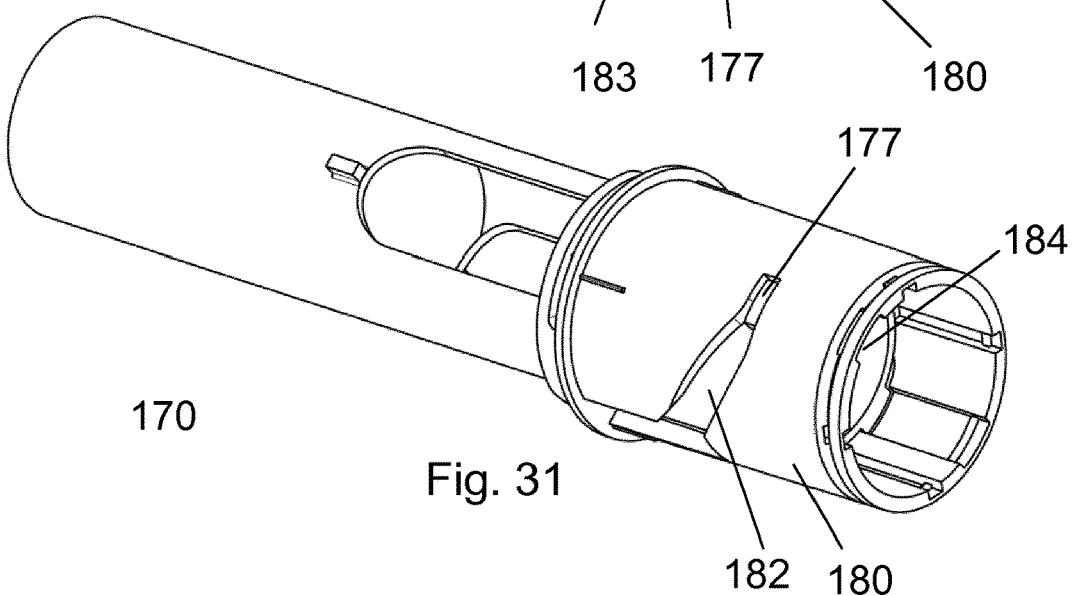
FIG. 31 show the engagement between the axially movable shield and the initiator in a ready to inject state according to the second embodiment of the invention.

In order to equalize the pressure inside the cartridge 120, the user, as in the first embodiment, rotates the axially movable shield 170 from the position depicted in FIG. 30 to the position depicted in FIG. 31. This rotation brings the knop 177 through the helical track 182 with the result that the axially movable shield 170 moves helically in the proximal direction.

Figure 33:
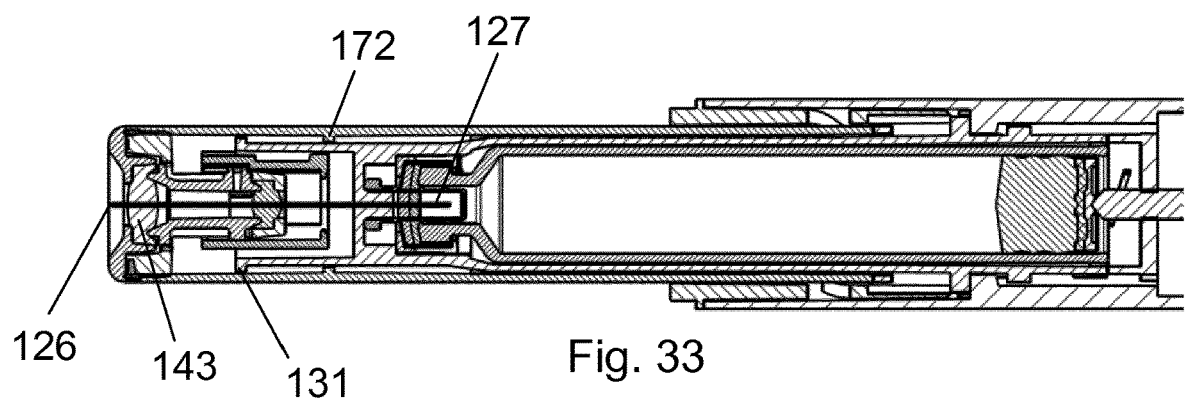
FIG. 33 show a cross sectional view of front end of the injection device during the equalizing of the pressure inside the cartridge according to the second embodiment of the invention.

The position in which the pressure has been equalized is depicted in FIG. 33, which depict the axially movable shield 170 in the same position as in FIG. 31. The distal tip 126 of the needle cannula 120 has now been brought to a position just in front of the distal barrier 143 of the cleaning chamber 141.

At the same time the knop 177 has been brought into the second axil track 184 which means the needle shield is now unlocked and an injection can be performed.

Figure 34:
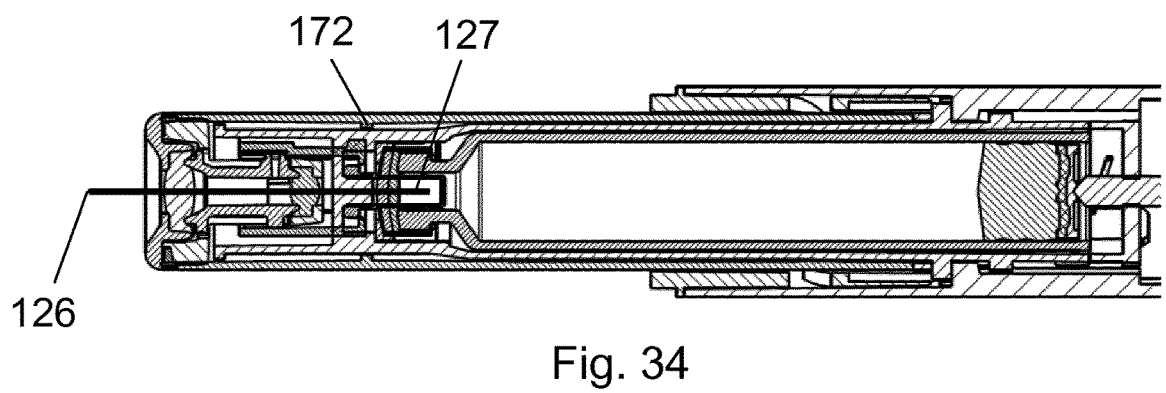
FIG. 34 show a cross sectional view of front end of the injection device during injection according to the second embodiment of the invention.
Figure 35:
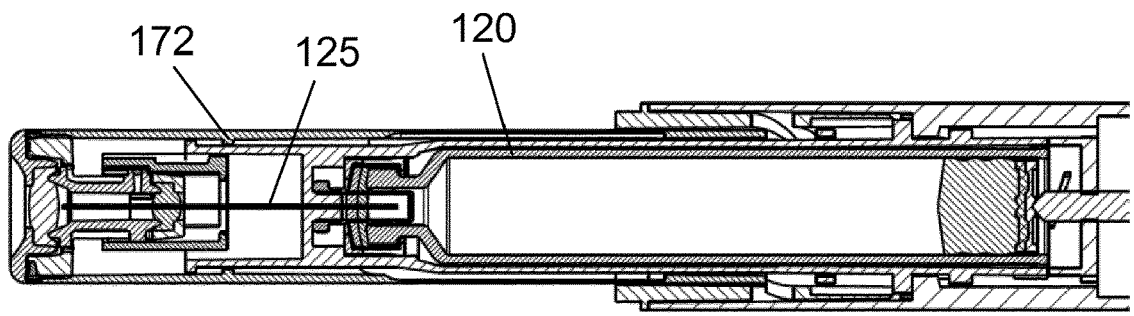
FIG. 35 show a cross sectional view of front end of the injection device before remounting of the removable cap according to the second embodiment of the invention.

The injection is performed by pressing the distal end of the axially movable shield 170 against the skin "S" of the user as disclosed in FIG. 34. The injection itself can be done manually or automatically as it is generally known.

Once the injection has been performed and the injection device is retracted from the skin "S" of the user the axially movable shield 170 is urged back to the position disclosed in FIG. 33 by a not-shown spring mechanism. From this position the user is able to rotate the axially movable shield 170 such that the knop 177 on the axially movable shield 170 is guided back to its previous position in the first axial track 183 as disclosed in FIG. 30. This end-of-injection position is disclosed in FIG. 35. In this position, the distal tip 126 is positioned inside the cleaning chamber 141 where it is rinsed before the next injection.

The next injection can henceforth be performed once the injection device has been unlocked by rotating the axially movable shield 170. Further, the axially movable shield 170 and the needle hub 130 are provided with windows, which windows, as in the first embodiment, are aligned when the injection device has been unlocked.

Some preferred embodiments have been shown in the foregoing, but it should be stressed that the invention is not limited to these, but may be embodied in other ways within the subject matter defined in the following claims.

The invention claimed is:

1. A prefilled injection pen for apportioning multiple set doses of a liquid drug comprising:
a housing assembly distally supporting a removable cap rotatably coupled to the housing assembly and which housing assembly further supports a piston rod drive system,
a non-replaceable cartridge embedded in the housing assembly and having an interior containing a preservative containing liquid drug, the interior being defined between a distal septum and a movable plunger abutting the piston rod drive system which comprises a piston rod for moving the plunger in the distal direction,
a needle cannula secured in a needle hub which needle cannula has a distal tip, a proximal end and a lumen there between,
an axially movable shield movable from an extended position covering at least the distal tip of the needle cannula to a retracted position in which at least the distal tip of the needle cannula is exposed and which axially movable shield carries a cleaning chamber for containing a quantum of the preservative containing liquid drug, and wherein,
the needle hub which engages the axially movable shield, is arranged to follow rotation of the removable cap and guided helically in relation to the housing assembly such that the needle hub is moved proximally upon rotation of the removable cap, and wherein the needle hub operates the axially movable shield to follow proximal movement of the needle hub in order to maintain the distal tip of the needle cannula inside the cleaning chamber as the needle hub and the axially movable shield carrying the cleaning chamber travels in the proximal direction.

2. The prefilled injection pen according to claim 1, wherein the housing assembly comprises a cartridge holder.

3. The prefilled injection pen according to claim 2, wherein the cartridge holder is provided with a radial protrusion engaging a helical track provided in the needle hub.

4. The prefilled injection pen according to claim 3, wherein the needle hub engages and moves the cartridge in the proximal direction upon movement of the radial protrusion in the helical track.

5. The prefilled injection pen according to claim 1, wherein the axially movable shield operates the needle hub such that the needle hub rotates simultaneously with the axially movable shield.

6. The prefilled injection pen according to claim 1, wherein the removable cap is provided with a helical cap track engaging protrusions provided on the housing assembly.

7. The prefilled injection pen according to claim 1, wherein the removable cap engages the axially movable shield such that a rotation of the removable cap is transferred to a rotation of the axially movable shield.

8. The prefilled injection pen according to claim 1, wherein the cartridge holder is provided with a helical flange for guiding the axially movable shield.

9. The prefilled injection pen according to claim 1, wherein the axially movable shield is provided with a first protrusion and a second protrusion.

10. The prefilled injection pen according to claim 9, wherein the first protrusion engages the helical flange on the cartridge holder such that the axially movable shield moves proximally when rotated.

11. The prefilled injection pen according to claim 9, wherein the second protrusion transfers rotation from the axially movable shield to the needle hub.

12. The prefilled injection pen according claim 1, wherein the axially movable shield is provided with a longitudinal slit.

13. The prefilled injection pen according to claim 1, wherein the housing assembly is provided with an internal rib.

14. The prefilled injection pen according to claim 13, wherein the longitudinal slit upon rotation of the axially movable shield is brought into alignment with the internal rib of the housing assembly thus allowing telescopic movement of the axially movable shield.

15. The prefilled injection pen according to claim 1, wherein the needle hub is locked to the housing assembly and provided with a longitudinal rib engaging a valve such that the valve is prevented from following rotation of the axially movable shield.

* * * * *